United States Patent
Kapeller-Libermann

(10) Patent No.: US 6,703,230 B2
(45) Date of Patent: Mar. 9, 2004

(54) 47174, A NOVEL HUMAN GLYCOSYLTRANSFERASE AND USES THEREOF

(75) Inventor: Rosana Kapeller-Libermann, Chestnut Hill, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 102 days.

(21) Appl. No.: 09/973,457

(22) Filed: Oct. 9, 2001

(65) Prior Publication Data

US 2002/0164746 A1 Nov. 7, 2002

Related U.S. Application Data

(60) Provisional application No. 60/238,849, filed on Oct. 6, 2000.

(51) Int. Cl.[7] .............................. C12Q 3/00; C12Q 1/48; C12N 9/00; C12N 15/09; C12N 9/10; C12N 1/20; C12N 15/00; C07K 1/00

(52) U.S. Cl. .............................. 435/193; 435/4; 435/15; 435/69.1; 435/183; 435/193; 435/226; 536/23.2; 514/789; 530/350

(58) Field of Search .............................. 435/4, 15, 41, 435/74, 183, 193, 226, 252.3, 320.1; 536/23.2; 530/350; 514/789

(56) References Cited

PUBLICATIONS

Shinya Toba, et al., "Brain–Specific Expression of a Novel Human UDP–GalNAc: Polypeptide N–Acetylgalactosaminyltransferase (GalNAc–T9)," *Biochemica et Biophysica Acta*, vol. 1493, (2000), pp. 264–268.

*Primary Examiner*—Manjunath Rao
(74) *Attorney, Agent, or Firm*—Millennium Pharmaceuticals, Inc.

(57) ABSTRACT

The invention provides isolated nucleic acids molecules, designated 47174 nucleic acid molecules, which encode novel glycosyltransferase family members. The invention also provides antisense nucleic acid molecules, recombinant expression vectors containing 47174 nucleic acid molecules, host cells into which the expression vectors have been introduced, and nonhuman transgenic animals in which a 47174 gene has been introduced or disrupted. The invention still further provides isolated 47174 proteins, fusion proteins, antigenic peptides and anti-47174 antibodies. Diagnostic methods utilizing compositions of the invention are also provided. The invention also provides methods of modulating pain or pain related disorders utilizing the compositions of the invention. Accordingly, methods of treating, preventing and/or diagnosing neurological disorders are disclosed.

14 Claims, 4 Drawing Sheets

```
Glycos_transf_2: domain 1 of 1, from 154 to 336: score 55.7, E = 1e-12
                *->sivIptYNeeadyLeelleSvlaqs.tledieiivvDDgSetDetve
                   s+v +  Ne+++ +++ ++Sv +  +  + e+i vDD+S + e++
       47174  154    SVVFIFVNEALSVILRSVHSVVNHTpSQLLKEVILVDDNSDNVELKF   200 iaedylderikeenpriiivirleensqGpaaArnkgirratGdsdyIlf
                   ++ y+    ++ +p  + ++r++++  G +Ar +g ++at    ++ f
       47174  201 NLDQYV----NKRYPGLVKIVRNSRRE-GLIRARLQGWKAATAP--VVGF   243

LDaDdiftpdklekLidyaeatdaavvlgaida.....yeyaegesnlyr
                   +Da+++f   ++ e+++++++ +++ +vl+aid  + +++e +++ + ++
       47174  244 FDAHVEFNTGWAEPALSRIREDRRRIVLPAIDNikystFEVQQYANA-AH   292 iaradterslfagllrktgrltgglelsfeigsnaiyrreafeelf<-*
                   ++++ ++  ++  +++   +r  g+ ++  +++++ + ++ +++e+f
       47174  293 GYNWGLWCMYIIPPQDWLDR--GDESAPIRTPAMIGCSFVVDREYF       336
```

Fig. 2

```
Alignments of top-scoring domains:
ricin_3: domain 1 of 1, from 465 to 595: score 32.5, E =9.8e-06
                 *>rgyfliiggntglCLdvngnsesksdGnpvglwdChgggnQlWkltY
                   +g ++ +   ++ CLd  +++++      + +l++Chg ++Ql +++
       47174   465   YGEVRNSK-ASAYCLDQGAEDGD-----RAILYPCHGMSSQLVRYS- 504 nesdgairi.........nsdlCLtvng...tvtlysCdgtdkgndnQk.
                   dg +  ++ +++      + +CL  +g+++  tl++C++    + + Q+
       47174   505 --ADGLLQLgplgstaflPDSKCLVDDGtgrMPTLKKCEDV--ARPTQRl 550

Wevnkdgcirnpknskkgvdsglc Ldvkdgn......kvqlwtcngsdap
                   W + ++g i+++          +g cL+v  +++ + +  +++  c+g
       47174   551 WDFTQSGPIVSR-------ATGRCLEVEMSKdanfglRLVVQRCSG---- 589 nQkWife<-*
                   QkW ++
       47174   590 -QKWMIR    595
```

Fig. 3

>2308 p99.2 (23) PAGT(3) // N-ACETYLGALACTOSAMINYLTRANSFERASE TRANSFERASE
    POLYPEPTIDE ACETYLGALACTOSAMINYLTRANFERASE UDP-GALNAC:POLYPEPTIDE
    GLYCOSYLTRANSFERASE PROTEIN-UDP PROTEIN-UDP N-
        LENGTH = 172

Score = 423 (154.0 bits), Expect = 4.7e-40, P = 4.7e-40
 Identities = 77/151 (50%), Positives = 104/151 (68%)

Query:   312  RGDESAPIRTPAMIGCSFVVDREYFGDIGLLDPGMEVYGGENVELGMRVWQCGGSMEVLP 371
              R D + PIR+P M G  F +++EYF ++G  DPGM+++GGEN+EL  RVWQCGG +E++P
Sbjct:    14  RKDPTDPIRSPTMAGGLFAINKEYFEELGTYDPGMDIWGGENLELSFRVWQCGGRLEIVP 73

Query:   372  CSRVAHIERTRKPYNNDIDYYAK----RNALRAAEVWMDDFKSHVYMAWNIPMSNPGVDF 427
              CS V H+ R R  PY         K    RN +R AEVWMDD+K + Y  + P +    DF
Sbjct:    74  CSHVGHVFRKRSPYTFPGKGSGKDVISRNTVRVAEVWMDDYKEYFYK--HNPQARKVRDF 131

Query:   428  GDVSERLALRQRLKCRSFKWYLENVYPEMRV 458
              GD+SER  LR++L+C+SFKWYLENVYP++ V
Sbjct:   132  GDISERKELREKLQCKSFKWYLENVYPDLYV 162

Fig. 4

47174, A NOVEL HUMAN GLYCOSYLTRANSFERASE AND USES THEREOF

RELATED APPLICATIONS

This application claims priority to U.S. provisional application No. 60/238,849 filed on Oct. 6, 2000, the contents of which are incorporated herein by reference in their entirety.

BACKGROUND OF THE INVENTION

A great diversity of oligosaccharide structures and types of glycoconjugates is found in nature, and these are synthesized by a large number of glycosyltransferases. Glycosyltransferases catalyze the synthesis of glycoconjugates, including glycolipids, glycoproteins, and polysaccharides, by transferring an activated mono- or oligosaccharide residue to an existing acceptor molecule for the initiation or elongation of the carbohydrate chain. A catalytic reaction is believed to involve the recognition of both the donor and acceptor by suitable domains, as well as the catalytic site of the enzyme (Amado et al. (1999) *Biochim Biophys Acta* 1473:35–53; Kapitonov et al. (1999) *Glycobiology* 9:961–78).

Because the glycosylation reaction is highly specific with respect to both the configuration of the sugar residue and the site of the addition, it is expected that unique domain structures for substrate recognition and nucleotide-sugar binding are located within the enzyme molecule. Evidence indicates that formation of many glycosidic linkages is covered by large homologous glycosyltransferase gene families, and that the existence of multiple enzyme isoforms provides a degree of redundancy as well as a higher level of regulation of the glycoforms synthesized (Kapitonov et al. (1999) *Glycobiology* 9:961–78).

Glycosylation is the principal chemical modification to proteins as they pass through Golgi vesicles. Glycosyltransferases of the Golgi do not possess an obvious sequence homology which would suggest a common Golgi retention signal. However, they are all membrane proteins and share type II topology, consisting of an amino terminal cytoplasmic tail, a signal anchor transmembrane domain, a stem region, and a large luminal catalyitc domain. The membrane-spanning domain and its flanking regions contain necessary and sufficient information for Golgi retention of these enzymes (Jaskiewicz (1997) *Acta Biochim Pol* 44:173–9). ER localized glycosyltransferases can have either a type II topology, like the Golgi glycosyltransferases, or a type I topolgy, e.g., the N-terminus and catalytic domain inside the ER (Kapitonov et al. (1999) *Glycobiology* 9:961–78). Some glycosyltransferases are present on the cell surface and are thought to function as cell adhesion molecules by binding oligosaccharide substrates on adjacent cell surfaces or in the extracellular matrix. The best studied of these is beta 1,4-galactosyltransferase, which mediates sperm binding to the egg coat and selected cell interactions with the basal lamina (Shur (1993) *Curr Opin Cell Biol* 5:854–63).

SUMMARY OF THE INVENTION

The present invention is based, in part, on the discovery of a novel glycosyltransferase family member, referred to herein as "47174." The nucleotide sequence of a cDNA encoding 47174 is shown in SEQ ID NO:1, and the amino acid sequence of a 47174 polypeptide is shown in SEQ ID NO:2. In addition, the nucleotide sequence of the coding region is depicted in SEQ ID NO:3.

Accordingly, in one aspect, the invention features a nucleic acid molecule which encodes a 47174 protein or polypeptide, e.g., a biologically active portion of a 47174 protein. In a preferred embodiment the isolated nucleic acid molecule encodes a polypeptide having the amino acid sequence of SEQ ID NO:2. In other embodiments, the invention provides isolated 47174 nucleic acid molecules having the nucleotide sequence shown in SEQ ID NO:1 or SEQ ID In still other embodiments, the invention provides nucleic acid molecules that are substantially identical (e.g., naturally occurring allelic variants) to the nucleotide sequence shown in SEQ ID NO: 1 or SEQ ID NO:3 In other embodiments, the invention provides a nucleic acid molecule which hybridizes under a stringent hybridization condition described herein to a nucleic acid molecule comprising the nucleotide sequence of SEQ ID NO: 1 or SEQ ID NO:3, wherein the nucleic acid encodes a full length 47174 protein or an active fragment thereof.

In a related aspect, the invention further provides nucleic acid constructs that include a 47174 nucleic acid molecule described herein. In certain embodiments, the nucleic acid molecules of the invention are operatively linked to native or heterologous regulatory sequences. Also included, are vectors and host cells containing the 47174 nucleic acid molecules of the invention e.g., vectors and host cells suitable for producing 47174 nucleic acid molecules and polypeptides. The invention thus also provides vectors and host cells that express the 47174 nucleic acid molecules and polypeptides of the invention. Transgenic animals expressing 47174 nucleic acid molecules and polypeptides of the invention also are provided.

In another related aspect, the invention provides nucleic acid fragments suitable as primers or hybridization probes for the detection of 47174-encoding nucleic acids.

In still another related aspect, isolated nucleic acid molecules that are antisense to a 47174 encoding nucleic acid molecule are provided.

In a preferred embodiment, the 47174 nucleic acid has a nucleotide sequence identical to, or substantially identical to, SEQ ID NO:1 or 3. In other embodiments, the 47174 nucleic acid is a fragment of at least 50, 100, 150, 200, 250, 300, 350, 400, 450, 500, 1000, 1500, 2000, 2500, 2550, or more contiguous nucleotides of SEQ ID NO:1 or 3. In another aspect, the invention features antibodies and antigen-binding fragments thereof, that react with, or more preferably specifically bind 47174 polypeptides.

In another embodiment, the invention provides 47174 polypeptides. Preferred polypeptides are 47174 proteins having a 47174-associated activity, e.g., a glycosyltransferase activity as described herein. In another aspect, the invention features, 47174 polypeptides, and biologically active or antigenic fragments thereof that are useful, e.g., as reagents or targets in assays applicable to treatment and diagnosis of 47174 mediated or related disorders.

In other embodiments, the invention provides 47174 polypeptides, e.g., a 47174 polypeptide having the amino acid sequence shown in SEQ ID NO:2; an amino acid sequence that is substantially identical to the amino acid sequence shown in SEQ ID NO:2; or an amino acid sequence encoded by a nucleic acid molecule having a nucleotide sequence which hybridizes under a stringent hybridization condition described herein to a nucleic acid molecule comprising the nucleotide sequence of SEQ ID NO:1 or SEQ ID NO:3, wherein the nucleic acid encodes a full length 47174 protein or an active fragment thereof.

In a preferred embodiment, the 47174 polypeptide has an amino acid sequence identical to, or substantially identical to, SEQ ID NO:2. In other embodiments, the 47174 polypeptide is a fragment of at least 15, 20, 50, 100, 150, 200, 300, 400, 500, 600, or more contiguous amino acids of SEQ ID NO:2.

In a related aspect, the invention provides 47174 polypeptides or fragments operatively linked to non-47174 polypeptides to form fusion proteins.

In another aspect, the invention provides methods of screening for agents, e.g., compounds, that modulate the expression or activity of the 47174 polypeptides or nucleic acids, e.g., compounds that modulate neurological activity or function, e.g., central nervous system (CNS) development or function, or that modulate the normal, or aberrant or altered pain response.

In a preferred embodiment, the effect of an agent, e.g., a compound, on the pain response is evaluated by an analgesic test, e.g., the hot plate test, tail flick test, writhing test, paw pressure test, all electric stimulation test, tail withdrawal test, or formalin test.

In a preferred embodiment, the agent, e.g., compound, inhibits 47174 activity.

In a preferred embodiment, the agent, e.g., compound, increases endogenous levels of a 47174 substrate, e.g., glycoconjugates, including glycolipids, glycoproteins, and polysaccharides.

In still another aspect, the invention provides a process for modulating 47174 polypeptide or nucleic acid expression or activity, e.g. using the screened compounds. In certain embodiments, the methods involve treatment of conditions related to aberrant, e.g., decreased or increased expression of the 47174 polypeptides or nucleic acids, such as conditions involving neurological, e.g., CNS, function, e.g., pain response, aberrant or altered pain response, pain related disorders.

In still another aspect, the invention features a method of modulating (e.g., enhancing or inhibiting) an activity of a 47174-expressing cell (e.g., a neural (e.g., a CNS) cell, or a kidney cell), or a response, e.g., a neurological response (e.g., a pain or nociceptive response) in a subject. The method includes contacting the 47174-expressing cell with, or administered to the subject, an agent, e.g., a compound, that modulates the activity or expression of a 47174 polypeptide or nucleic acid, in an amount effective to modulate the activity or the response.

The agent, e.g., the compound, and the 47174-polypeptide or nucleic acid can be contacted in vitro or ex vivo. In other embodiments, the contacting step is effected in vivo in a subject, e.g., as part of a therapeutic or prophylactic protocol. The contacting or administering step(s) can be repeated.

In a preferred embodiment, the agent modulates (e.g., increases or decreases) glycosyltransferase activity. In other embodiments, the agent modulates (e.g., increases or decreases) expression of the 47174 nucleic acid by, e.g., modulating transcription, mRNA stability, etc.

In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a growth factor, e.g., a neurotrophic or neurotropic factor (e.g., BDNF, NGF, NT-3), a hormone, etc. In those embodiments where cell killing is desired the therapeutic moiety is selected from a cytotoxin, a cytotoxic agent and a radioactive metal ion.

In additional preferred embodiments, the agent is an antisense molecule, a ribozyme, a triple helix molecule, or a 47174 nucleic acid, or any combination thereof.

In a preferred embodiment, the agent is administered in combination with a growth factor, e.g., a neurotrophic or neurotropic factor (e.g., BDNF, NGF, NT-3), a hormone. In other embodiments, the agent is a cytotoxic agent.

In a preferred embodiment, the cell, e.g., the 47174-expressing cell, is a central or peripheral nervous system cell, e.g., a cortical or a hypothalamic cell; a spinal cord cell (e.g., a cell in the DRG); a cell in an area involved in pain control, e.g., a cell in the substantia gelatinosa of the spinal cord, or a cell in the periaqueductal gray matter.

Preferably, the subject is a human, e.g., a patient with a neurological disorder, e.g., a neurodegenerate disorder, a CNS dysfunction, pain or a pain-associated disorder disclosed herein. For example, the subject can be a patient with pain elicited from tissue injury, e.g., inflammation, infection, ischemia; pain associated with musculoskeletal disorders, e.g., joint pain; tooth pain; headaches, e.g., migrane; pain associated with surgery; pain related to inflammation, e.g., irritable bowel syndrome; or chest pain. The subject can be a patient with complex regional pain syndrome (CRPS), reflex sympathetic dystrophy (RSD), causalgia, neuralgia, central pain and dysesthesia syndrome, carotidynia, neurogenic pain, refractory cervicobrachial pain syndrome, myofascial pain syndrome, craniomandibular pain dysfunction syndrome, chronic idiopathic pain syndrome, Costen's pain-dysfunction, acute chest pain syndrome, gynecologic pain syndrome, patellofemoral pain syndrome, anterior knee pain syndrome, recurrent abdominal pain in children, colic, low back pain syndrome, neuropathic pain, phantom pain from amputation, phantom tooth pain, or pain asymbolia. The subject can be a cancer patient, e.g., a patient with brain cancer, bone cancer, or prostate cancer. In other embodiments, the subject is a non-human animal, e.g., an experimental animal, e.g., an arthritic rat model of chronic pain, a chronic constriction injury (CCI) rat model of neuropathic pain, or a rat model of unilateral inflammatory pain by intraplantar injection of Freund's complete adjuvant (FCA).

In another aspect, the invention features a method of treating or preventing, in a subject, a 47174-associated disorder. The method includes administering to the subject, e.g., a subject at risk of, or afflicted with, a 47174-associated disorder, an agent, e.g., a compound as described herein, that modulates the activity or expression of a 47174 polypeptide or nucleic acid, in an amount effective to treat or prevent the disorder.

In a preferred embodiment, the disorder is neurological, e.g., a neurodegenerative, disorder, a CNS disorder, e.g., a brain or spinal cord related disorder, or a pain or a pain related disorder. In other embodiments, the disorder is a renal disorder.

In a preferred embodiment, the subject is a subject as described herein, e.g., a human, e.g., a patient with a neurological disorder, e.g., a neurodegenerate disorder, or a subject suffering from pain or a pain-associated disorder disclosed herein. In other embodiments, the subject is a patient having a renal disorder.

In still another aspect, the invention features a method for evaluating the efficacy of a treatment of a disorder, e.g., a disorder disclosed herein, in a subject. The method includes treating a subject with a protocol under evaluation; assessing the expression of a 47174 nucleic acid or 47174 polypeptide, such that a change in the level of 47174 nucleic acid or 47174 polypeptide after treatment, relative to the level before treatment, is indicative of the efficacy of the treatment of the disorder.

In a preferred embodiment, the disorder is neurological, e.g., a neurodegenerative, disorder, a CNS disorder, e.g., a brain or spinal cord related disorder, or a pain or a pain related disorder. In other embodiments, the disorder is a renal disorder.

In a preferred embodiment, the subject is a subject as described herein, e.g., a human, e.g., a patient with a neurological disorder, e.g., a neurodegenerate disorder, or a subject suffering from pain or a pain-associated disorder disclosed herein. In other embodiments, the subject is a patient having a renal disorder.

The invention also features a method of diagnosing a disorder, e.g., a disorder disclosed herein, in a subject. The method includes evaluating the expression or activity of a 47174 nucleic acid or a 47174 polypeptide, such that, a difference in the level of 47174 nucleic acid or 47174 polypeptide relative to a normal subject or a cohort of normal subjects is indicative of the disorder.

In a preferred embodiment, the disorder is neurological, e.g., a neurodegenerative, disorder, a CNS disorder, e.g., a brain or spinal cord related disorder, or a pain or a pain related disorder. In other embodiments, the disorder is a renal disorder.

In a preferred embodiment, the subject is a subject as described herein, e.g., a human, e.g., a patient with a neurological disorder, e.g., a neurodegenerate disorder, or a subject suffering from pain or a pain-associated disorder disclosed herein. In other embodiments, the subject is a patient having a renal disorder.

In a preferred embodiment, the evaluating step occurs in vitro or ex vivo. For example, a sample, e.g., a blood sample, is obtained from the subject.

In a preferred embodiment, the evaluating step occurs in vivo. For example, by administering to the subject a detectably labeled agent that interacts with the 47174 nucleic acid or polypeptide, such that a signal is generated relative to the level of activity or expression of the 47174 nucleic acid or polypeptide.

The invention also provides assays for determining the activity of or the presence or absence of 47174 polypeptides or nucleic acid molecules in a biological sample, including for disease diagnosis.

In further aspect, the invention provides assays for determining the presence or absence of a genetic alteration in a 47174 polypeptide or nucleic acid molecule, including for disease diagnosis.

In yet another aspect, the invention features a method for identifying an agent, e.g., a compound, which modulates the activity of a 47174 polypeptide, e.g., a 47174 polypeptide as described herein, or the expression of a 47174 nucleic acid, e.g., a 47174 nucleic acid as described herein, including contacting the 47174 polypeptide or nucleic acid with a test agent (e.g., a test compound); and determining the effect of the test compound on the activity of the 47174 polypeptide or nucleic acid to thereby identify a compound which modulates the activity of the 47174 polypeptide or nucleic acid.

In a preferred embodiment, the activity of the 47174 polypeptide is a glycosyltransferase activity, e.g., the synthesis of a glycoconjugate, e.g., a glycolipid, glycoprotein, orolysaccharides.

In a preferred embodiment, the activity of the 47174 polypeptide is modulation of a neural response, e.g., a pain response.

In preferred embodiments, the agent is a peptide, a phosphopeptide, a small molecule, e.g., a member of a combinatorial library, or an antibody, or any combination thereof.

In additional preferred embodiments, the agent is an antisense, a ribozyme, or a triple helix molecule, or a 47174 nucleic acid, or any combination thereof.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 47174 molecule. In one embodiment, the capture probe is a nucleic acid, e.g., a probe complementary to a 47174 nucleic acid sequence. In another embodiment, the capture probe is a polypeptide, e.g., an antibody specific for 47174 polypeptides. Also featured is a method of analyzing a sample by contacting the sample to the aforementioned array and detecting binding of the sample to the array.

Other features and advantages of the invention will be apparent from the following detailed description, and from the claims.

DESCRIPTION OF THE DRAWINGS

FIG. 2 depicts an alignment of the glycosyltransferase group 2 domain of human 47174 with a consensus amino acid sequence derived from a hidden Markov model. The upper sequence is the consensus amino acid sequence (SEQ ID NO:4), while the lower amino acid sequence corresponds to amino acids 154 to 336 of SEQ ID NO:2.

FIG. 3 depicts an alignment of the ricin group 3 domain of human 47174 with a consensus amino acid sequence derived from a hidden Markov model. The upper sequence is the consensus amino acid sequence (SEQ ID NO:5), while the lower amino acid sequence corresponds to amino acids 465 to 595 of SEQ ID NO:2.

FIG. 4 depicts an alignment of the N-acetylgalatosaminyltransferase domain of human 47174 with a consensus amino acid sequence derived from a hidden Markov model. The lower sequence is the consensus amino acid sequence (SEQ ID NO:6), while the upper amino acid sequence corresponds to amino acids 312 to 458 of SEQ ID NO:2.

SEQUENCE LISTING

<160> NUMBER OF SEQ ID NOS: 6

Figure 1:
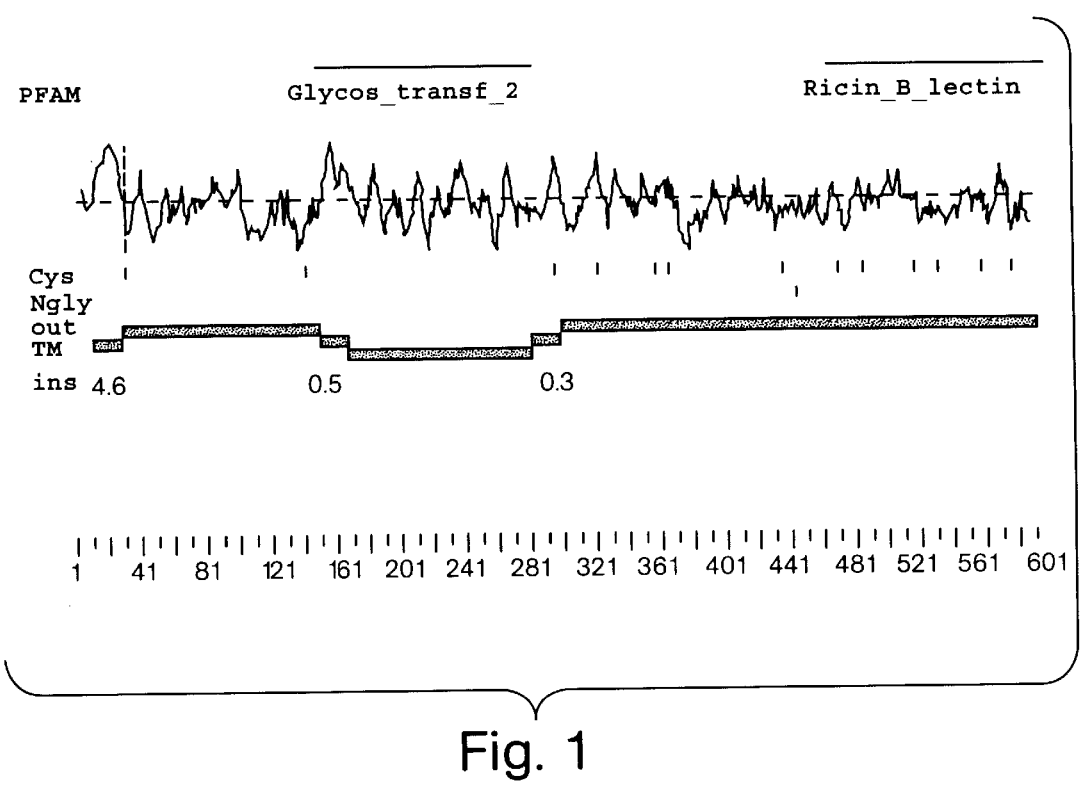
FIG. 1 depicts a hydropathy plot of human 47174. Relative hydrophobic residues are shown above the dashed horizontal line, and relative hydrophilic residues are below the dashed horizontal line. The cysteine residues (cys) are indicated by short vertical lines just below the hydropathy trace. The numbers corresponding to the amino acid sequence of human 47174 are indicated. Polypeptides of the invention include fragments that include: all or a part of a hydrophobic sequence (a sequence above the dashed line); or all or part of a hydrophilic fragment (a sequence below the dashed line). Other fragments include a cysteine residue.

<210> SEQ ID NO 1
<211> LENGTH: 2572
<212> TYPE: DNA
<213> ORGANISM: Homo sapiens
<220> FEATURE:
<221> NAME/KEY: CDS
<222> LOCATION: (325)...(2133)

<400> SEQUENCE: 1

```
gcgccgcccg cccgcgcctt ccccgccgcc ccccggcgcc cccggccccc ctcaccgctc      60
cccggggcgg ggccgcgccc tctgagcggg ggatgccggc cgcgcccgc gaccccagcc      120 ccgggcagcc ctctgcgctc tgggggaccc ccggcggccg tggcccggcg cgctgagctg     180
gtgctgaagg acagctccg gccgagcccc gcagcccccg cagccccggg cggctcatgg      240
tccccgaagc cgaagctgaa gcccaggccc gggcggggat gctggggatg ccccgcgggt     300
gaggcccccg ctgcagccgt gttc atg gcg gtg gcc agg aag atc cga act         351
                              Met Ala Val Ala Arg Lys Ile Arg Thr
                                1               5 ttg ctg acg gtg aac atc ctg gtg ttc gtg ggc atc gtc ctg ttc tcc       399
Leu Leu Thr Val Asn Ile Leu Val Phe Val Gly Ile Val Leu Phe Ser
 10              15                  20                  25 gtg tac tgc cgc ctg cag ggc cgc tcc cag gag ctc gtg cgc atc gtg       447
Val Tyr Cys Arg Leu Gln Gly Arg Ser Gln Glu Leu Val Arg Ile Val
             30                  35                  40 agc ggc gac cgc cgg gtg cgc agc cga cac gcc aag gtg ggc acg ctg       495
Ser Gly Asp Arg Arg Val Arg Ser Arg His Ala Lys Val Gly Thr Leu
         45                  50                  55 ggg gac cgt gag gcc atc ctg cag cgc ctg gac cac ctg gag gag gtg       543
Gly Asp Arg Glu Ala Ile Leu Gln Arg Leu Asp His Leu Glu Glu Val
     60                  65                  70 gtc tac aac cag ctc aac ggc ctt gcc aag ccc atc ggc ctg gtg gag       591
Val Tyr Asn Gln Leu Asn Gly Leu Ala Lys Pro Ile Gly Leu Val Glu
 75                  80                  85 ggg cca gga ggc ctg ggc cag ggt ggc ttg gcg gcc acc ctg cgt gat       639
Gly Pro Gly Gly Leu Gly Gln Gly Gly Leu Ala Ala Thr Leu Arg Asp
 90              95                 100                 105 gac ggc cag gag gcg gaa ggc aag tat gag gag tac ggc tac aac gct       687
Asp Gly Gln Glu Ala Glu Gly Lys Tyr Glu Glu Tyr Gly Tyr Asn Ala
                110                 115                 120 cag ctc agc gac cgc atc tcc ctc gat cgg agc atc ccc gac tac cgg       735
Gln Leu Ser Asp Arg Ile Ser Leu Asp Arg Ser Ile Pro Asp Tyr Arg
            125                 130                 135 ccc aga aag tgc aga cag atg agc tac gcc cag gac ctg ccc cag gtc       783
Pro Arg Lys Cys Arg Gln Met Ser Tyr Ala Gln Asp Leu Pro Gln Val
        140                 145                 150 tcc gtg gtc ttc atc ttc gtg aat gag gcg ctg tcg gtc atc ctg cgc       831
Ser Val Val Phe Ile Phe Val Asn Glu Ala Leu Ser Val Ile Leu Arg
    155                 160                 165 tcc gtg cac agc gtg gtc aac cac acg ccc tcc cag ctc ctc aag gag       879
Ser Val His Ser Val Val Asn His Thr Pro Ser Gln Leu Leu Lys Glu
170                 175                 180                 185 gtc atc ctg gtg gac gac aac agt gac aac gtg gaa ctc aag ttc aat       927
Val Ile Leu Val Asp Asp Asn Ser Asp Asn Val Glu Leu Lys Phe Asn
                190                 195                 200 ctg gac cag tac gtc aac aag cgg tac cca ggc ctc gtg aag att gtc       975
Leu Asp Gln Tyr Val Asn Lys Arg Tyr Pro Gly Leu Val Lys Ile Val
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 205 |     |     |     |     | 210 |     |     |     |     | 215 |     |     |     |      |
| cgc | aac | agc | cgg | cgg | gaa | gga | ctg | atc | cgc | gcg | cgg | ctg | cag | ggc | tgg | 1023 |
| Arg | Asn | Ser | Arg | Arg | Glu | Gly | Leu | Ile | Arg | Ala | Arg | Leu | Gln | Gly | Trp |      |
|     |     | 220 |     |     |     |     | 225 |     |     |     |     | 230 |     |     |     |      |
| aag | gcg | gcc | acc | gcc | cca | gtc | gtc | ggc | ttc | ttt | gat | gcc | cac | gtc | gag | 1071 |
| Lys | Ala | Ala | Thr | Ala | Pro | Val | Val | Gly | Phe | Phe | Asp | Ala | His | Val | Glu |      |
|     |     | 235 |     |     |     |     | 240 |     |     |     |     | 245 |     |     |     |      |
| ttc | aac | acg | ggc | tgg | gcc | gag | ccc | gca | ctg | tcg | cgg | atc | cga | gag | gac | 1119 |
| Phe | Asn | Thr | Gly | Trp | Ala | Glu | Pro | Ala | Leu | Ser | Arg | Ile | Arg | Glu | Asp |      |
| 250 |     |     |     |     | 255 |     |     |     |     | 260 |     |     |     |     | 265 |      |
| cgg | cgt | cgc | atc | gtg | ctg | cca | gcc | atc | gac | aac | atc | aag | tac | agc | acg | 1167 |
| Arg | Arg | Arg | Ile | Val | Leu | Pro | Ala | Ile | Asp | Asn | Ile | Lys | Tyr | Ser | Thr |      |
|     |     |     |     | 270 |     |     |     |     | 275 |     |     |     |     | 280 |     |      |
| ttt | gag | gtg | cag | cag | tat | gcg | aac | gcc | gcc | cat | ggc | tac | aac | tgg | ggc | 1215 |
| Phe | Glu | Val | Gln | Gln | Tyr | Ala | Asn | Ala | Ala | His | Gly | Tyr | Asn | Trp | Gly |      |
|     |     |     |     | 285 |     |     |     |     | 290 |     |     |     |     | 295 |     |      |
| ctc | tgg | tgc | atg | tac | atc | atc | ccc | ccg | cag | gac | tgg | ctg | gac | cgc | ggc | 1263 |
| Leu | Trp | Cys | Met | Tyr | Ile | Ile | Pro | Pro | Gln | Asp | Trp | Leu | Asp | Arg | Gly |      |
|     |     |     | 300 |     |     |     |     | 305 |     |     |     |     | 310 |     |     |      |
| gac | gag | tca | gca | ccc | atc | agg | acc | cca | gcc | atg | atc | ggc | tgc | tcc | ttc | 1311 |
| Asp | Glu | Ser | Ala | Pro | Ile | Arg | Thr | Pro | Ala | Met | Ile | Gly | Cys | Ser | Phe |      |
|     |     | 315 |     |     |     |     | 320 |     |     |     |     | 325 |     |     |     |      |
| gta | gtg | gac | cgc | gag | tac | ttc | gga | gac | att | ggg | ctg | ctg | gac | ccc | ggc | 1359 |
| Val | Val | Asp | Arg | Glu | Tyr | Phe | Gly | Asp | Ile | Gly | Leu | Leu | Asp | Pro | Gly |      |
| 330 |     |     |     |     | 335 |     |     |     |     | 340 |     |     |     |     | 345 |      |
| atg | gag | gtg | tat | ggc | ggc | gag | aac | gta | gaa | ctg | ggc | atg | agg | gtg | tgg | 1407 |
| Met | Glu | Val | Tyr | Gly | Gly | Glu | Asn | Val | Glu | Leu | Gly | Met | Arg | Val | Trp |      |
|     |     |     |     | 350 |     |     |     |     | 355 |     |     |     |     | 360 |     |      |
| cag | tgt | ggc | ggc | agc | atg | gag | gtg | ctg | ccc | tgc | tcc | cgc | gtg | gcc | cac | 1455 |
| Gln | Cys | Gly | Gly | Ser | Met | Glu | Val | Leu | Pro | Cys | Ser | Arg | Val | Ala | His |      |
|     |     |     |     | 365 |     |     |     |     | 370 |     |     |     |     | 375 |     |      |
| atc | gag | cgc | acc | agg | aag | ccc | tac | aac | aac | gac | att | gac | tac | tac | gcc | 1503 |
| Ile | Glu | Arg | Thr | Arg | Lys | Pro | Tyr | Asn | Asn | Asp | Ile | Asp | Tyr | Tyr | Ala |      |
|     |     |     | 380 |     |     |     |     | 385 |     |     |     |     | 390 |     |     |      |
| aag | cgc | aac | gcc | ctg | cgc | gcc | gcc | gag | gtg | tgg | atg | gat | gac | ttc | aag | 1551 |
| Lys | Arg | Asn | Ala | Leu | Arg | Ala | Ala | Glu | Val | Trp | Met | Asp | Asp | Phe | Lys |      |
|     | 395 |     |     |     |     | 400 |     |     |     |     | 405 |     |     |     |     |      |
| tcc | cac | gtg | tac | atg | gcc | tgg | aac | atc | ccc | atg | tcg | aac | cca | ggg | gtg | 1599 |
| Ser | His | Val | Tyr | Met | Ala | Trp | Asn | Ile | Pro | Met | Ser | Asn | Pro | Gly | Val |      |
| 410 |     |     |     |     | 415 |     |     |     |     | 420 |     |     |     |     | 425 |      |
| gac | ttc | ggg | gac | gtg | tct | gag | agg | ctg | gcc | ctg | cgt | cag | agg | ctg | aag | 1647 |
| Asp | Phe | Gly | Asp | Val | Ser | Glu | Arg | Leu | Ala | Leu | Arg | Gln | Arg | Leu | Lys |      |
|     |     |     |     | 430 |     |     |     |     | 435 |     |     |     |     | 440 |     |      |
| tgt | cgc | agc | ttc | aag | tgg | tac | ctg | gag | aac | gtg | tac | ccg | gag | atg | agg | 1695 |
| Cys | Arg | Ser | Phe | Lys | Trp | Tyr | Leu | Glu | Asn | Val | Tyr | Pro | Glu | Met | Arg |      |
|     |     |     |     | 445 |     |     |     |     | 450 |     |     |     |     | 455 |     |      |
| gtc | tac | aac | aac | acc | ctc | acg | tac | gga | gag | gtg | aga | aac | agc | aaa | gcc | 1743 |
| Val | Tyr | Asn | Asn | Thr | Leu | Thr | Tyr | Gly | Glu | Val | Arg | Asn | Ser | Lys | Ala |      |
|     |     |     | 460 |     |     |     |     | 465 |     |     |     |     | 470 |     |     |      |
| agt | gcc | tac | tgt | ctg | gac | cag | gga | gcg | gag | gac | ggc | gac | cgg | gcg | atc | 1791 |
| Ser | Ala | Tyr | Cys | Leu | Asp | Gln | Gly | Ala | Glu | Asp | Gly | Asp | Arg | Ala | Ile |      |
|     | 475 |     |     |     |     | 480 |     |     |     |     | 485 |     |     |     |     |      |
| ctc | tac | ccc | tgc | cac | ggg | atg | tcc | tcc | cag | ctg | gtg | cgg | tac | agc | gct | 1839 |
| Leu | Tyr | Pro | Cys | His | Gly | Met | Ser | Ser | Gln | Leu | Val | Arg | Tyr | Ser | Ala |      |
| 490 |     |     |     |     | 495 |     |     |     |     | 500 |     |     |     |     | 505 |      |
| gac | ggc | ctg | ctg | cag | ctg | ggg | cct | ctg | ggc | tcc | aca | gcc | ttc | ttg | cct | 1887 |
| Asp | Gly | Leu | Leu | Gln | Leu | Gly | Pro | Leu | Gly | Ser | Thr | Ala | Phe | Leu | Pro |      |
|     |     |     |     | 510 |     |     |     |     | 515 |     |     |     |     | 520 |     |      |
| gac | tcc | aag | tgt | ctg | gtg | gat | gac | ggc | acg | ggc | cgc | atg | ccc | acc | ctg | 1935 |

-continued

```
Asp Ser Lys Cys Leu Val Asp Asp Gly Thr Gly Arg Met Pro Thr Leu
        525                 530                 535 aag aag tgt gag gat gtg gcg cgg cca aca cag cgg ctg tgg gac ttc    1983
Lys Lys Cys Glu Asp Val Ala Arg Pro Thr Gln Arg Leu Trp Asp Phe
        540                 545                 550 acc cag agt ggc ccc att gtg agc cgg gcc acg ggc cgc tgc ctg gag    2031
Thr Gln Ser Gly Pro Ile Val Ser Arg Ala Thr Gly Arg Cys Leu Glu
        555                 560                 565 gtg gag atg tcc aaa gat gcc aac ttt ggg ctc cgg ctg gta gta cag    2079
Val Glu Met Ser Lys Asp Ala Asn Phe Gly Leu Arg Leu Val Val Gln
570                 575                 580                 585 agg tgc tcg ggg cag aag tgg atg atc aga aac tgg atc aaa cac gca    2127
Arg Cys Ser Gly Gln Lys Trp Met Ile Arg Asn Trp Ile Lys His Ala
                590                 595                 600 cgg cac tgaccccacc tccgcccgga ccccacaga cctcgggaag gcgctgggcc      2183
Arg His gagccagtgt ggctgagtga ccggggtgtg cccggcagac acagcaggac agggctctat  2243
gtgcggccag acagcagag gctgaggggc cggggtgtgg ctgagtgacc aggtgtcac    2303 ccactgcatc tggagtacag cttctcctag gacaggcggc tctacccgag ggagggcgtc  2363
tggggacagt gatgccaact caaacacgtg ccttctccac ggtatctcct ggccaggctg  2423
ctgggacagc cgccgcctct gcatgtacca cagccccca cgcccatag ggaggccaag    2483 ccccggacca tgcaccaggc tgcaccctgg tgtcttccac ccgcaggcct cccatgctcc  2543
aagcagcctc ccccagcact tgcggccgc                                    2572

<210> SEQ ID NO 2
<211> LENGTH: 603
<212> TYPE: PRT
<213> ORGANISM: Homo sapiens

<400> SEQUENCE: 2

Met Ala Val Ala Arg Lys Ile Arg Thr Leu Leu Thr Val Asn Ile Leu
 1               5                  10                  15

Val Phe Val Gly Ile Val Leu Phe Ser Val Tyr Cys Arg Leu Gln Gly
                20                  25                  30

Arg Ser Gln Glu Leu Val Arg Ile Val Ser Gly Asp Arg Arg Val Arg
        35                  40                  45

Ser Arg His Ala Lys Val Gly Thr Leu Gly Asp Arg Glu Ala Ile Leu
    50                  55                  60

Gln Arg Leu Asp His Leu Glu Glu Val Val Tyr Asn Gln Leu Asn Gly
65                  70                  75                  80

Leu Ala Lys Pro Ile Gly Leu Val Glu Gly Pro Gly Gly Leu Gly Gln
                85                  90                  95

Gly Gly Leu Ala Ala Thr Leu Arg Asp Asp Gly Gln Glu Ala Glu Gly
            100                 105                 110

Lys Tyr Glu Glu Tyr Gly Tyr Asn Ala Gln Leu Ser Asp Arg Ile Ser
        115                 120                 125

Leu Asp Arg Ser Ile Pro Asp Tyr Arg Pro Arg Lys Cys Arg Gln Met
    130                 135                 140

Ser Tyr Ala Gln Asp Leu Pro Gln Val Ser Val Val Phe Ile Phe Val
145                 150                 155                 160

Asn Glu Ala Leu Ser Val Ile Leu Arg Ser Val His Ser Val Val Asn
                165                 170                 175

His Thr Pro Ser Gln Leu Leu Lys Glu Val Ile Leu Val Asp Asp Asn
            180                 185                 190
```

-continued

```
Ser Asp Asn Val Glu Leu Lys Phe Asn Leu Asp Gln Tyr Val Asn Lys
            195                 200                 205

Arg Tyr Pro Gly Leu Val Lys Ile Val Arg Asn Ser Arg Arg Glu Gly
        210                 215                 220

Leu Ile Arg Ala Arg Leu Gln Gly Trp Lys Ala Thr Ala Pro Val
225                 230                 235                 240

Val Gly Phe Phe Asp Ala His Val Glu Phe Asn Thr Gly Trp Ala Glu
                245                 250                 255

Pro Ala Leu Ser Arg Ile Arg Glu Asp Arg Arg Ile Val Leu Pro
            260                 265                 270

Ala Ile Asp Asn Ile Lys Tyr Ser Thr Phe Glu Val Gln Gln Tyr Ala
        275                 280                 285

Asn Ala Ala His Gly Tyr Asn Trp Gly Leu Trp Cys Met Tyr Ile Ile
        290                 295                 300

Pro Pro Gln Asp Trp Leu Asp Arg Gly Asp Glu Ser Ala Pro Ile Arg
305                 310                 315                 320

Thr Pro Ala Met Ile Gly Cys Ser Phe Val Val Asp Arg Glu Tyr Phe
                325                 330                 335

Gly Asp Ile Gly Leu Leu Asp Pro Gly Met Glu Val Tyr Gly Gly Glu
            340                 345                 350

Asn Val Glu Leu Gly Met Arg Val Trp Gln Cys Gly Gly Ser Met Glu
        355                 360                 365

Val Leu Pro Cys Ser Arg Val Ala His Ile Glu Arg Thr Arg Lys Pro
    370                 375                 380

Tyr Asn Asn Asp Ile Asp Tyr Tyr Ala Lys Arg Asn Ala Leu Arg Ala
385                 390                 395                 400

Ala Glu Val Trp Met Asp Asp Phe Lys Ser His Val Tyr Met Ala Trp
                405                 410                 415

Asn Ile Pro Met Ser Asn Pro Gly Val Asp Phe Gly Asp Val Ser Glu
            420                 425                 430

Arg Leu Ala Leu Arg Gln Arg Leu Lys Cys Arg Ser Phe Lys Trp Tyr
        435                 440                 445

Leu Glu Asn Val Tyr Pro Glu Met Arg Val Tyr Asn Asn Thr Leu Thr
450                 455                 460

Tyr Gly Glu Val Arg Asn Ser Lys Ala Ser Ala Tyr Cys Leu Asp Gln
465                 470                 475                 480

Gly Ala Glu Asp Gly Asp Arg Ala Ile Leu Tyr Pro Cys His Gly Met
                485                 490                 495

Ser Ser Gln Leu Val Arg Tyr Ser Ala Asp Gly Leu Leu Gln Leu Gly
            500                 505                 510

Pro Leu Gly Ser Thr Ala Phe Leu Pro Asp Ser Lys Cys Leu Val Asp
        515                 520                 525

Asp Gly Thr Gly Arg Met Pro Thr Leu Lys Lys Cys Glu Asp Val Ala
    530                 535                 540

Arg Pro Thr Gln Arg Leu Trp Asp Phe Thr Gln Ser Gly Pro Ile Val
545                 550                 555                 560

Ser Arg Ala Thr Gly Arg Cys Leu Glu Val Glu Met Ser Lys Asp Ala
                565                 570                 575

Asn Phe Gly Leu Arg Leu Val Val Gln Arg Cys Ser Gly Gln Lys Trp
            580                 585                 590

Met Ile Arg Asn Trp Ile Lys His Ala Arg His
        595                 600
```

<210> SEQ ID NO 3
<211> LENGTH: 1812
<212> TYPE: DNA
<213> ORGANISM: Homo sapiens

<400> SEQUENCE: 3

| | | | | | | |
|---|---|---|---|---|---|---|
| atggcggtgg | ccaggaagat | ccgaactttg | ctgacggtga | acatcctggt | gttcgtgggc | 60 |
| atcgtcctgt | tctccgtgta | ctgccgcctg | cagggccgct | cccaggagct | cgtgcgcatc | 120 |
| gtgagcggcg | accgccgggt | gcgcagccga | cacgccaagg | tgggcacgct | ggggacccgt | 180 |
| gaggccatcc | tgcagcgcct | ggaccacctg | gaggaggtgg | tctacaacca | gctcaacggc | 240 |
| cttgccaagc | ccatcggcct | ggtggagggg | ccaggaggcc | tgggccaggg | tggcttggcg | 300 |
| gccaccctgc | gtgatgacgg | ccaggaggcg | gaaggcaagt | atgaggagta | cggctacaac | 360 |
| gctcagctca | gcgaccgcat | ctccctcgat | cggagcatcc | ccgactaccg | gcccagaaag | 420 |
| tgcagacaga | tgagctacgc | ccaggacctg | ccccaggtct | ccgtggtctt | catcttcgtc | 480 |
| aatgaggcgc | tgtcggtcat | cctgcgctcc | gtgcacagcg | tggtcaacca | cacgccctcc | 540 |
| cagctcctca | aggaggtcat | cctggtggac | acaacagtg | acaacgtgga | actcaagttc | 600 |
| aatctggacc | agtacgtcaa | caagcggtac | ccaggcctcg | tgaagattgt | ccgcaacagc | 660 |
| cggcgggaag | gactgatccg | cgcgcggctg | cagggctgga | aggcggccac | cgccccagtc | 720 |
| gtcggcttct | tgatgcccca | cgtcgagttc | aacacgggct | gggccgagcc | cgcactgtcg | 780 |
| cggatccgag | aggaccggcg | tcgcatcgtg | ctgccagcca | tcgacaacat | caagtacagc | 840 |
| acgtttgagg | tgcagcagta | tgcgaacgcc | gcccatggct | acaactgggg | cctctggtgc | 900 |
| atgtacatca | tcccccgca | ggactggctg | gaccgcggcg | acgagtcagc | acccatcagg | 960 |
| accccagcca | tgatcggctg | ctccttcgta | gtggaccgcg | agtacttcgg | agacattggg | 1020 |
| ctgctggacc | ccggcatgga | ggtgtatggc | ggcgagaacg | tagaactggg | catgagggtg | 1080 |
| tggcagtgtg | gcggcagcat | ggaggtgctg | ccctgctccc | gcgtggccca | catcgagcgc | 1140 |
| accaggaagc | cctacaacaa | cgacattgac | tactacgcca | gcgcaacgc | cctgcgcgcc | 1200 |
| gccgaggtgt | ggatggatga | cttcaagtcc | cacgtgtaca | tggcctggaa | catccccatg | 1260 |
| tcgaacccag | gggtggactt | cggggacgtg | tctgagaggc | tggccctgcg | tcagaggctg | 1320 |
| aagtgtcgca | gcttcaagtg | gtacctggag | aacgtgtacc | cggagatgag | ggtctacaac | 1380 |
| aacaccctca | cgtacggaga | ggtgagaaac | agcaaagcca | gtgcctactg | tctgaccag | 1440 |
| ggagcggagg | acggcgaccg | ggcgatcctc | taccccctgcc | acgggatgtc | ctcccagctg | 1500 |
| gtgcggtaca | cgctgacgg | cctgctgcag | ctggggcctc | tgggctccac | agccttcttg | 1560 |
| cctgactcca | agtgtctggt | ggatgacggc | acgggccgca | tgcccaccct | gaagaagtgt | 1620 |
| gaggatgtgg | cgcggccaac | acagcggctg | tgggacttca | cccagagtgg | ccccattgtg | 1680 |
| agccgggcca | cgggccgctg | cctggaggtg | gagatgtcca | agatgccaa | ctttgggctc | 1740 |
| cggctggtgg | tacagaggtg | ctcggggcag | aagtggatga | tcagaaactg | gatcaaacac | 1800 |
| gcacggcact | ga | | | | | 1812 |

<210> SEQ ID NO 4
<211> LENGTH: 187
<212> TYPE: PRT
<213> ORGANISM: Artificial Sequence
<220> FEATURE:
<223> OTHER INFORMATION: Consensus sequence

<400> SEQUENCE: 4

```
Ser Ile Val Ile Pro Thr Tyr Asn Glu Glu Ala Asp Tyr Leu Glu Glu
  1               5                  10                 15

Leu Leu Glu Ser Val Leu Ala Gln Ser Thr Leu Glu Asp Ile Glu Ile
             20                  25                  30

Ile Val Val Asp Asp Gly Ser Glu Thr Asp Glu Thr Val Glu Ile Ala
             35                  40                  45

Glu Asp Tyr Leu Asp Glu Arg Ile Lys Glu Glu Asn Pro Arg Ile Ile
         50                  55                  60

Ile Val Ile Arg Leu Glu Glu Asn Ser Gln Gly Pro Ala Ala Ala Arg
 65                  70                  75                  80

Asn Lys Gly Ile Arg Arg Ala Thr Gly Asp Ser Asp Tyr Ile Leu Phe
                 85                  90                  95

Leu Asp Ala Asp Asp Ile Phe Thr Pro Asp Lys Leu Glu Lys Leu Ile
                100                 105                 110

Asp Tyr Ala Glu Ala Thr Asp Ala Ala Val Val Leu Gly Ala Ile Asp
             115                 120                 125

Ala Tyr Glu Tyr Ala Glu Gly Glu Ser Asn Leu Tyr Arg Ile Ala Arg
         130                 135                 140

Ala Asp Thr Glu Arg Ser Leu Phe Ala Gly Leu Leu Arg Lys Thr Gly
145                 150                 155                 160

Arg Leu Thr Gly Gly Leu Glu Leu Ser Phe Glu Ile Gly Ser Asn Ala
                165                 170                 175

Ile Tyr Arg Arg Glu Ala Phe Glu Glu Leu Phe
                180                 185

<210> SEQ ID NO 5
<211> LENGTH: 135
<212> TYPE: PRT
<213> ORGANISM: Artificial Sequence
<220> FEATURE:
<223> OTHER INFORMATION: Consensus sequence

<400> SEQUENCE: 5

Arg Gly Tyr Phe Leu Ile Ile Gly Gly Asn Thr Gly Leu Cys Leu Asp
  1               5                  10                 15

Val Asn Gly Asn Ser Glu Ser Lys Ser Asp Gly Asn Pro Val Gln Leu
             20                  25                  30

Trp Asp Cys His Gly Gly Asn Gln Leu Trp Lys Leu Thr Tyr Asn
             35                  40                  45

Glu Ser Asp Gly Ala Ile Arg Ile Asn Ser Asp Leu Cys Leu Thr Val
         50                  55                  60

Asn Gly Thr Val Thr Leu Tyr Ser Cys Asp Gly Thr Asp Lys Gly Asn
 65                  70                  75                  80

Asp Asn Gln Lys Trp Glu Val Asn Lys Asp Gly Thr Ile Arg Asn Pro
                 85                  90                  95

Lys Asn Ser Lys Lys Gly Val Asp Ser Gly Leu Cys Leu Asp Val Lys
                100                 105                 110

Asp Gly Asn Lys Val Gln Leu Trp Thr Cys Asn Gly Ser Asp Ala Pro
             115                 120                 125

Asn Gln Lys Trp Ile Phe Glu
         130                 135

<210> SEQ ID NO 6
<211> LENGTH: 149
<212> TYPE: PRT
<213> ORGANISM: Artificial Sequence
```

-continued

<220> FEATURE:
<223> OTHER INFORMATION: Consensus sequence

<400> SEQUENCE: 6

```
Arg Lys Asp Pro Thr Asp Pro Ile Arg Ser Pro Thr Met Ala Gly Gly
1               5                   10                  15

Leu Phe Ala Ile Asn Lys Glu Tyr Phe Glu Glu Leu Gly Thr Tyr Asp
            20                  25                  30

Pro Gly Met Asp Ile Trp Gly Gly Glu Asn Leu Glu Leu Ser Phe Arg
        35              40                  45

Val Trp Gln Cys Gly Gly Arg Leu Glu Ile Val Pro Cys Ser His Val
    50              55                  60

Gly His Val Phe Arg Lys Arg Ser Pro Tyr Thr Phe Pro Gly Lys Gly
65                  70                  75                  80

Ser Gly Lys Asp Val Ile Ser Arg Asn Thr Val Arg Val Ala Glu Val
            85                  90                  95

Trp Met Asp Asp Tyr Lys Glu Tyr Phe Tyr Lys His Asn Pro Gln Ala
            100                 105                 110

Arg Lys Val Arg Asp Phe Gly Asp Ile Ser Glu Arg Lys Glu Leu Arg
            115                 120                 125

Glu Lys Leu Gln Cys Lys Ser Phe Lys Trp Tyr Leu Glu Asn Val Tyr
    130                 135                 140

Pro Asp Leu Tyr Val
145
```

DETAILED DESCRIPTION

The human 47174 sequence (Example 1; SEQ ID NO:1), which is approximately 2572 nucleotides long including untranslated regions, contains a predicted methionine-initiated coding sequence of about 1812 nucleotides (nucleotides 325–2136 of SEQ ID NO:1; SEQ ID NO:3). The coding sequence encodes a 603 amino acid protein (SEQ ID NO:2). Human 47174 protein of SEQ ID NO:2 includes an amino-terminal hydrophobic amino acid sequence, consistent with a signal sequence of about 30 amino acids (from amino acid 1 to about amino acid 28 of SEQ ID NO:2), which upon protease removal results in the production of the mature protein.

This mature protein form is approximately 575 amino acid residues in length (from about amino acid 29 to amino acid 603 of SEQ ID NO:2). Human 47174 contains the following regions or other structural features: a glycosyltransferase group 2 domain (PFAM Accession PF00535) located at about amino acid residues 154 to 336 of SEQ ID NO:2; and a ricin domain at about amino acids residues 465–595 of SEQ ID NO:2.

The 47174 protein further includes the following domains: one an asparagine N-glycosylation site (PS00001) located at about amino acids 2–5; 10 predicted Protein Kinase C phosphorylation sites (PS00005) located at about amino acids 102–104, 124–126, 220–222, 381–383, 431–433, 444–446, 531–533, 536–538, 547–549 and 564–566 of SEQ ID NO:2; five predicted Casein Kinase II phosphorylation sites (PS00006) located at about amino 56–59, 102–105, 132–135, 220–223 and 280–283 of SEQ ID NO:2; two predicted tyrosine kinase phosphorylation sites (PS00007) located at about amino acids 113–119 and 446–453 of SEQ ID NO:2; four predicted N-myristoylation sites (PS00008) located at about amino acids 93–98, 224–229, 424–429 and 481–486 of SEQ ID NO:2; one predicted RGD Cell attachment site (PS00016) located at about amino acids 312–314 of SEQ ID NO:2; and a predicted leucine zipper motif located at about amino acids 16–37 of SEQ ID NO:2.

For general information regarding PFAM identifiers, PS prefix and PF prefix domain identification numbers, refer to Sonnhammer et al. (1997) Protein 28:405–420.

The 47174 protein contains a significant number of structural characteristics in common with members of the glycosyltransferase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

A 47174 polypeptide can include a "glycosyltransferase domain" or regions homologous with a "glycosyltransferase domain." A 47174 polypeptide can further include a "ricin domain" or regions homologous with a "ricin domain".

As used herein, the term "glycosyltransferase" includes a protein or polypeptide which is capable of catalyzing the synthesis of glycoconjugates, including glycolipids, glycoproteins, and polysaccharides, by transferring an activated mono- or oligosaccharide residue to an existing acceptor molecule for the initiation or elongation of the carbohydrate chain. The acceptor can be a lipid, a protein, a heterocyclic compound, or another carbohydrate residue.

Glycosyltransferases can be divided into numerous subfamilies based upon their specificity for sugar moieties and acceptor molecules. The glycosyltransferase domain of human 47174 bears similarity to a subfamily designated "group 2" glycosyltransferases. These enzymes comprise a diverse subfamily, whose members transfer sugar from UDP-glucose, UDP-N-acetyl-galactosamine, GDP-mannose or CDP-abequose, to a range of substrates including cellulose, dolichol phosphate and teichoic acids. Based on the sequence similarities, the 47174 molecule of the present invention is predicted to have similar biological activities as glycosyltransferase family members.

Glycosyltransferases play roles in diverse cellular processes. For example, the major target of the natural IgM and IgG antibodies during hyperacute xenograft rejection is the terminal carbohydrate epitope Gal alpha(1,3)Gal, formed by the alpha 1,3galactosyl transferase, which places a terminal galactose residue in an alpha-linkage to another galactose (Sandrin et al. (1994) *Immunol Rev* 141:169–90). Additionally, UDP-galactose:ceramide galactosyltransferase is the enzyme responsible for the biosynthesis of galactosylceramide, a molecule thought to play a critical role in myelin formation, signal transduction, viral and microbial adhesion, and oligodendrocyte development (Kapitonov et al. (1999) *Glycobiology* 9:961–78). As 47174 mRNA is highly expressed in brain cortex and hypothalamus, the 47174 molecules of the invention are likely to play a role in the development and/or function of the nervous system, e.g., the brain, e.g., in modulating the pain response.

Glycosylation of glycoproteins and glycolipids is one of many molecular changes that accompany malignant transformation. GlcNAc-branched N-glycans and terminal Lewis antigen sequences have been observed to increase in some cancers, and to correlate with poor prognosis (Dennis et al. (1999) *Biochim Biophys Acta* 1473:21–34). Cellular membrane over-expression and shedding of acidic glycosphingolipids into the interstitial spaces and blood of cancer patients may play a central role in increased tumour cell growth, lack of immune cell recognition and neovascularization and could represent a molecular target for cancer therapy (Fish (1996) *Med Hypotheses* 46:140–44).

Thus, the 47174 molecules of the present invention may be involved in: 1) brain function, e.g., pain response, oligodendrocyte development, or myelin formation; 2) the transfer of an activated sugar residue to an acceptor molecule; 3) the processing, folding, and secretion of proteins; 4) the modulation of tumor cell growth and invasion; 5) signal transduction; 6) viral and microbial adhesion; 7) sperm-egg binding; 8) evasion of immune detection; 9) xenograft rejection; and 10) the ability to antagonize or inhibit, competitively or non-competitively, any of 1–10.

As used herein, the term "glycosyltransferase domain" includes an amino acid sequence of about 100–250 amino acid residues in length and having a bit score for the alignment of the sequence to the glycosyltransferase domain (HMM) of at least 30. Preferably, a glycosyltransferase domain includes at least about 120–220 amino acids, more preferably about 120–200 amino acid residues, or about 130–180 amino acids and has a bit score for the alignment of the sequence to the glycosyltransferase domain (HMM) of at least 50 or greater. Glycosyltransferase domains (HMM) have been assigned numerous PFAM Accession Numbers, including PF00534 (group 1) and PF00535 (group 2). An alignment of the glycosyltransferase domain (amino acids 154 to 336 of SEQ ID NO:2) of human 47174 with a consensus amino acid sequence (group 2 glycosyltransferases) derived from a hidden Markov model is depicted in FIG. 2.

In a preferred embodiment, the 47174 polypeptide or protein has a "glycosyltransferase domain" or a region which includes at least about 120–220 more preferably about 120–200 or 130–180 amino acid residues and has at least about 70% 80% 90% 95%, 99%, or 100% homology with a "glycosyltransferase domain," e.g., the glycosyltransferase domain of human 47174 (e.g., residues 154 to 336 of SEQ ID NO:2).

A 47174 family member can additionally include a ricin domain. Ricin is a heterodimer composed of two subunits, a lectin and a glycosidase, and it binds to terminal galactose residues on the cell surface via the lectin. Following endocytosis of the intact molecule, a disulfide bond linking the two subunits is cleaved, and only the glycosidase subunit enters the cytoplasm, where it inhibits cytoplasmic protein synthesis by catalyzing the cleavage of the 28S rRNA. Ricin B-chain (RTB) is a galactose-specific lectin that folds into two globular domains, each of which binds a single galactoside. The two binding sites are structurally similar and both contain a conserved tripeptide kink and an aromatic residue that comprises a sugar-binding platform. As used herein, the term "ricin" includes a protein or polypeptide which is capable of inhibiting cytoplasmic protein synthesis by catalyzing the cleavage of the 28S rRNA. For example, ricin has been utilized as an anticancer agent.

As used herein, the term "ricin domain" includes an amino acid sequence of about 100–250 amino acid residues in length and having a bit score for the alignment of the sequence to the ricin domain (HMM) of at least 30. Preferably, a ricin domain includes at least about 120–220 amino acids, more preferably about 120–200 amino acid residues, or about 130–180 amino acids and has a bit score for the alignment of the sequence to the ricin domain (HMM) of at least 50 or greater. An alignment of the ricin domain (amino acids 465–595 of SEQ ID NO:2) of human 47174 with a consensus amino acid sequence (Ricin B lectin) derived from a hidden Markov model is depicted in FIG. 3.

In a preferred embodiment, the 47174 polypeptide or protein has a "ricin domain" or a region which includes at least about 120–220 more preferably about 120–200 or 130–180 amino acid residues and has at least about 70% 80% 90% 95%, 99%, or 100% homology with a "ricin domain," e.g., the ricin domain of human 47174 (e.g., residues 465 to 595 of SEQ ID NO:2).

To identify the presence of a "glycosyltransferase" or a "ricin" domain in a 47174 protein sequence, and make the determination that a polypeptide or protein of interest has a particular profile, the amino acid sequence of the protein can be searched against a database of HMMs (e.g., the Pfam database, release 2.1) using the default parameters (online at sanger.ac.uk/Software/Pfam/HMM_search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al.(1990) *Meth Enzymol* 183:146–159; Gribskov et al.(1987) *Proc Natl Acad Sci USA* 84:4355–4358; Krogh et al.(1994) *J Mol Biol.* 235:1501–1531; and Stultz et al. (1993) *Protein Sci* 2:305–314, the contents of which are incorporated herein by reference. A search was performed against the HMM database resulting in the identification of a "glycosyltransferase"

domain in the amino acid sequence of human 47174 at about residues 154 to 336 of SEQ ID NO:2 and a ricin domain at about residues 465–595 of SEQ ID NO:2.

As the 47174 polypeptides of the invention may modulate 47174-mediated activities, they may be useful as or for developing novel diagnostic and therapeutic agents for 47174-mediated or related disorders, as described below.

As used herein, a "47174 activity", "biological activity of 47174" or "functional activity of 47174", refers to an activity exerted by a 47174 protein, polypeptide or nucleic acid molecule on e.g., a 47174-responsive cell or on a 47174 substrate, e.g., a lipid, protein, heterocyclic compound, or carbohydrate residue, as determined in vivo or in vitro. In one embodiment, a 47174 activity is a direct activity, such as an association with a 47174 target molecule. A "target molecule" or "binding partner" is a molecule with which a 47174 protein binds or interacts in nature, e.g., a lipid, protein, heterocyclic compound, or carbohydrate residue to which the 47174 protein attaches a carbohydrate moiety. A 47174 activity can also be an indirect activity, e.g., a cellular signaling activity mediated by interaction of the 47174 protein with a 47174 ligand.

47174 mRNA is expressed in brain cortex and hypothalamus and in kidney. As other glycosyltransferases are known to be involved in, e.g., oligodendrocyte development and myelin formation, it suggests a role for 47174 in, e.g., CNS function and/or development. Thus, the 47174 molecules can act as novel diagnostic targets and therapeutic agents in conditions related to CNS function, e.g., neurodegenerative disorders, neural development and maintenance, oligodendrocyte development and maintenance, myelin formation and maintenance, or pain response.

Animal models of pain response that may be useful as assays in the methods described herein include, but are not limited to, axotomy, the cutting or severing of an axon; chronic constriction injury (CCI), a model of neuropathic pain which involves ligation of the sciatic nerve in rodents, e.g., rats; or intraplantar Freund's adjuvant injection as a model of arthritic pain. Other animal models of pain response known in the art are described in, e.g., ILAR Journal (1999) Volume 40, Number 3 (entire issue).

As the 47174 polypeptides of the invention may modulate 47174-mediated activities, they may be useful for developing novel diagnostic and therapeutic agents for 47174-mediated or related disorders. For example, the 47174 molecules can act as novel diagnostic targets and therapeutic agents controlling CNS function or related disorders. Examples of glycosyltransferase associated disorders in which the 47174 molecules of the invention may be directly or indirectly involved include CNS related disorders, e.g., aberrant oligodendrocyte development, myelin formation or pain response.

Thus, the 47174 molecules can act as novel diagnostic targets and therapeutic agents for neurological, e.g., brain or glial, disorders. Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, *Varicalla-zoster* virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Examples of pain conditions include, but are not limited to, pain elicited during various forms of tissue injury, e.g., inflammation, infection, and ischemia; pain associated with musculoskeletal disorders, e.g., joint pain, or arthritis; tooth pain; headaches, e.g., migrane; pain associated with surgery; pain related to inflammation, e.g., irritable bowel syndrome; chest pain; or hyperalgesia, e.g., excessive sensitivity to pain (described in, for example, Fields (1987) *Pain*, New York:McGraw-Hill). Other examples of pain disorders or pain syndromes include, but are not limited to, complex regional pain syndrome (CRPS), reflex sympathetic dystrophy (RSD), causalgia, neuralgia, central pain and dysesthesia syndrome, carotidynia, neurogenic pain, refractory cervicobrachial pain syndrome, myofascial pain syndrome, craniomandibular pain dysfunction syndrome, chronic idiopathic pain syndrome, Costen's pain-dysfunction, acute chest pain syndrome, nonulcer dyspepsia, interstitial cystitis, gynecologic pain syndrome, patellofemoral pain syndrome, anterior knee pain syndrome, recurrent abdominal pain in children, colic, low back pain syndrome, neuropathic pain, phantom pain from amputation, phantom tooth pain, or pain asymbolia (the inability to feel pain). Other examples of pain conditions include pain induced by parturition, or post partum pain.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypemephroma, adenocarcinoma of kidney), which includes urothelial carcinomas of renal pelvis.

The 47174 protein, fragments thereof, and derivatives and other variants of the sequence in SEQ ID NO:2 thereof are collectively referred to as "polypeptides or proteins of the invention" or "47174 polypeptides or proteins." Nucleic acid molecules encoding such polypeptides or proteins are collectively referred to as "nucleic acids of the invention" or "47174 nucleic acids." 47174 molecules refer to 47174 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1–6.3.6, which is incorporated by reference. Aqueous and nonaqueous methods are described in that reference and either can be used. Specific hybridization conditions referred to herein are as follows: 1) low stringency hybridization conditions in 6×sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID NO:1 or SEQ ID NO:3, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 47174 protein, preferably a mammalian 47174 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 47174 protein having less than about 30%, 20%, 10% and more preferably 5% (by dry weight), of non-47174 protein (also referred to herein as a "contaminating protein"), or of chemical precursors or non-47174 chemicals. When the 47174 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 47174 (e.g., the sequence of SEQ ID NO:1 or 3) without abolishing or more preferably, without substantially altering a biological activity, whereas an "essential" amino acid residue results in such a change. For example, amino acid residues that are conserved among the polypeptides of the present invention, e.g., those present in the glycosyltransferase domain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 47174 protein is preferably replaced with another amino acid residue from the same side chain family. Alternatively, in another embodiment, mutations can be introduced randomly along all or part of a 47174 coding sequence, such as by saturation mutagenesis, and the resultant mutants can be screened for 47174 biological activity to identify mutants that retain activity. Following mutagenesis of SEQ ID NO:1 or SEQ ID NO:3, the encoded protein can be expressed recombinantly and the activity of the protein can be determined.

As used herein, a "biologically active portion" of a 47174 protein includes a fragment of a 47174 protein that participates in an interaction between a 47174 molecule and a non-47174 molecule. Biologically active portions of a 47174 protein include peptides comprising amino acid sequences sufficiently homologous to or derived from the amino acid sequence of the 47174 protein, e.g., the amino acid sequence shown in SEQ ID NO:2, which include fewer amino acids than the full length 47174 proteins, and exhibit at least one activity of a 47174 protein. Typically, biologically active portions comprise a domain or motif with at least one activity of the 47174 protein, e.g., glycosyltransferase activity. A biologically active portion of a 47174 protein can be a polypeptide which is, for example, 10, 25, 50, 100, 200 or more amino acids in length. Biologically active portions of a 47174 protein can be used as targets for developing agents which modulate a 47174 mediated activity, e.g., a glycosyltransferase activity.

Particularly preferred 47174 polypeptides of the present invention have an amino acid sequence substantially identical to the amino acid sequence of SEQ ID NO:2. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:2 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:1 or 3 are termed substantially identical.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 20%, 30%, preferably at least 40%, more preferably at least 50%, even more preferably at least 60%, and even more preferably at least 70%, 80%, 90%, 100% of the length of the reference sequence (e.g., when aligning a second sequence to the 47174 amino acid sequence of SEQ ID NO:2 having 206 amino acid residues (the glycosyltransferase domain), at least 40, 60, preferably at least 80, more preferably at least 100, even more preferably at least 120, and even more preferably at least 140, 160, or 180 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J Mol Biol* (48):444–453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS* 4:11–17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul et al. (1990) *J Mol Biol* 215:403–10. BLAST nucleotide searches can be performed with the NBLAST program, score=100, wordlength=12 to obtain nucleotide sequences homologous to 47174 nucleic acid molecules of the invention. BLAST protein searches can be performed with the XBLAST program, score=50, wordlength=3 to obtain amino acid sequences homologous to 47174 protein molecules of the invention. To obtain gapped alignments for comparison purposes, Gapped BLAST can be utilized as described in Altschul et al. (1997) *Nucleic Acids Res* 25(17):3389–3402. When utilizing BLAST and Gapped BLAST programs, the default parameters of the respective programs (e.g., XBLAST and NBLAST) can be used. See, e.g., the NCBI web site at ncbi.nlm.nih.gov.

"Misexpression or aberrant expression," as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, can refer to a mammal, e.g., a human, or to an experimental or animal or disease model, e.g., a rodent model of pain, e.g., an arthritic rat, a CCI rodent, or an axotomized rodent. The subject can also be a non-human animal, e.g., a horse, cow, goat, or other domestic animal.

A "purified preparation of cells," as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a 47174 polypeptide described herein, e.g., a full length 47174 protein or a fragment thereof, e.g., a biologically active portion of 47174 protein. Also included is a nucleic acid fragment suitable for use as a hybridization probe, which can be used, e.g., to identify a nucleic acid molecule encoding a polypeptide of the invention, 47174 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or a portion of the nucleotide sequence. In one embodiment, the nucleic acid molecule includes sequences encoding the human 47174 protein (i.e., "the coding region" of SEQ ID NO:1, as shown in SEQ ID NO:3), as well as 5' untranslated sequences. Alternatively, the nucleic acid molecule can include only the coding region of SEQ ID NO:1 (e.g., SEQ ID NO:3) and, e.g., no flanking sequences which normally accompany the subject sequence. In another embodiment, the nucleic acid molecule encodes a sequence corresponding to a fragment of the protein from about amino acid 154 to 336.

In another embodiment, an isolated nucleic acid molecule of the invention includes a nucleic acid molecule which is a complement of the nucleotide sequence shown in SEQ ID NO:1 or SEQ ID NO:3, or a portion of any of these nucleotide sequences. In other embodiments, the nucleic acid molecule of the invention is sufficiently complementary to the nucleotide sequence shown in SEQ ID NO:1 or SEQ ID NO:3, such that it can hybridize to the nucleotide sequence shown in SEQ ID NO:1 or 3, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1 or SEQ ID NO:3, or a portion, preferably of the same length, of any of these nucleotide sequences.

47174 Nucleic Acid Fragments

A nucleic acid molecule of the invention can include only a portion of the nucleic acid sequence of SEQ ID NO:1 or 3. For example, such a nucleic acid molecule can include a fragment which can be used as a probe or primer or a fragment encoding a portion of a 47174 protein, e.g., an immunogenic or biologically active portion of a 47174 protein. A fragment can comprise those nucleotides of SEQ ID NO:1, which encode a glycosyltransferase domain of human 47174. The nucleotide sequence determined from the cloning of the 47174 gene allows for the generation of probes and primers designed for use in identifying and/or cloning other 47174 family members, or fragments thereof, as well as 47174 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein.

Nucleic acid fragments can encode a specific domain or site described herein or fragments thereof, particularly fragments thereof which are at least 100 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 47174 nucleic acid fragment can include a sequence corresponding to a glycosyltransferase domain.

47174 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1 or SEQ ID NO:3, or of a naturally occurring allelic variant or mutant of SEQ ID NO:1 or SEQ ID NO:3.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes the glycosyltransferase domain of 47174 (from amino acids 154 to 336 of SEQ ID NO:2).

In another embodiment a set of primers is provided, e.g., primers suitable for use in a PCR, which can be used to amplify a selected region of a 47174 sequence, e.g., a domain, region, site or other sequence described herein. The primers should be at least 5, 10, or 50 base pairs in length and less than 100, or less than 200, base pairs in length. The primers should be identical, or differ by one base from a sequence disclosed herein or from a naturally occurring variant. For example, primers suitable for amplifying all or a portion of any of the following regions are provided: a glycosyltransferase domain from about amino acid 154 to 336 of SEQ ID NO:2; a ricin domain from about residues 465 to 595 of SEQ ID NO:2.

A nucleic acid fragment can encode an epitope bearing region of a polypeptide described herein.

A nucleic acid fragment encoding a "biologically active portion of a 47174 polypeptide" can be prepared by isolating a portion of the nucleotide sequence of SEQ ID NO:1 or 3, which encodes a polypeptide having a 47174 biological activity (e.g., the biological activities of the 47174 proteins are described herein), expressing the encoded portion of the 47174 protein (e.g., by recombinant expression in vitro) and assessing the activity of the encoded portion of the 47174 protein. For example, a nucleic acid fragment encoding a biologically active portion of 47174 includes a glycosyltransferase domain, e.g., amino acid residues about 154 to 336 of SEQ ID NO:2. A nucleic acid fragment encoding a biologically active portion of a 47174 polypeptide, may comprise a nucleotide sequence which is greater than 300 or more nucleotides in length.

In a preferred embodiment, a nucleic acid fragment includes a nucleotide sequence comprising nucleotides SEQ ID NO:1 or SEQ ID NO:3, or a portion thereof, wherein each portion is about 50 or longer nucleotides and hybridizes under stringent hybridization conditions to a nucleic acid molecule of SEQ ID NO:1, or SEQ ID NO:3.

In preferred embodiments, a nucleic acid fragment includes a nucleotide sequence which is at least 50, 100, 200, 300, 400, 500, 600, 700, 800, 900, 1000, 1100, 1200, 1208, 1300, 1400, 1500, 1600, 1700, 1800, 1900, 2000, 2100, 2200, 2300, 2400, 2500 or more nucleotides in length and hybridizes under stringent hybridization conditions to a nucleic acid molecule of SEQ ID NO:1, or SEQ ID NO:3.

In one preferred embodiment, the nucleic acid fragment includes at least 2 contiguous nucleotides from the sequence of amino acids 1 to 834 or 1634 to 2572 of SEQ ID NO:2.

In a preferred embodiment, a nucleic acid fragment differs by at least 1, 2, 3, 10, 20, or more nucleotides from a sequence described in WO00/58473, WO 01/53312, or WO 01/59063. Differences can include differing in length or sequence identity. For example, a nucleic acid fragment can: include one or more nucleotides from SEQ ID NO:1 or SEQ ID NO:3 located outside the region of nucleotides 835–1633, 1011–2217 or 244–1389 of SEQ ID NO:1; not include all of the nucleotides of a sequence of WO00/58473, WO 01/53312, or WO 01/59063, e.g., can be one or more nucleotides shorter (at one or both ends) than a sequence of WO00/58473, WO 01/53312, or WO 01/59063; or can differ by one or more nucleotides in the region of overlap.

47174 Nucleic Acid Variants

The invention further encompasses nucleic acid molecules that differ from the nucleotide sequence shown in SEQ ID NO:1 or SEQ ID NO:3. Such differences can be due to degeneracy of the genetic code (and result in a nucleic acid which encodes the same 47174 proteins as those encoded by the nucleotide sequence disclosed herein). In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2. If alignment is needed for this comparison the sequences should be aligned for maximum homology. "Looped" out sequences from deletions or insertions, or mismatches, are considered differences.

Nucleic acids of the invention can be chosen for having codons, which are preferred, or non preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1 or 3, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95%, 95–99%, or more identical to the nucleotide sequence shown in SEQ ID NO:2 or a fragment of this sequence. Such nucleic acid molecules can readily be identified as being able to hybridize under stringent conditions, to the nucleotide sequence encoding the amino acid sequence shown in SEQ ID NO: 2 or a fragment of the sequence. Nucleic acid molecules corresponding to orthologs, homologs, and allelic variants of the 47174 cDNAs of the invention can further be isolated by mapping to the same chromosome or locus as the 47174 gene.

Preferred variants include those that are correlated with glycosyltransferase activity.

Allelic variants of 47174, e.g., human 47174, include both functional and non-functional proteins. Functional allelic variants are naturally occurring amino acid sequence variants of the 47174 protein within a population that maintain the ability to bind substrates and hydrolyze them. Functional allelic variants will typically contain only conservative substitution of one or more amino acids of SEQ ID NO:2, or substitution, deletion or insertion of non-critical residues in non-critical regions of the protein. Non-functional allelic variants are naturally-occurring amino acid sequence variants of the 47174, e.g., human 47174, protein within a population that do not have the ability to bind and/or hydrolyze a substrate. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

Moreover, nucleic acid molecules encoding other 47174 family members and, thus, which have a nucleotide sequence which differs from the 47174 sequences of SEQ ID NO:1 or SEQ ID NO:3 are intended to be within the scope of the invention.

Antisense Nucleic Acid Molecules, Ribozymes and Modified 47174 Nucleic Acid Molecules In another aspect, the invention features, an isolated nucleic acid molecule which is antisense to 47174. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 47174 coding strand, or to only a portion thereof (e.g., the coding region of human 47174 corresponding to SEQ ID NO:3). In another embodiment, the antisense nucleic acid molecule is antisense to a "non-coding region" of the coding strand of a nucleotide sequence encoding 47174 (e.g., the 5' and 3' untranslated regions).

An antisense nucleic acid can be designed such that it is complementary to the entire coding region of 47174 mRNA, but more preferably is an oligonucleotide that is antisense to only a portion of the coding or noncoding region of 47174 mRNA. For example, the antisense oligonucleotide can be complementary to the region surrounding the translation start site of 47174 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 47174 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An alpha-anomeric nucleic acid molecule forms specific double-stranded hybrids with complementary RNA in which, contrary to the usual beta-units, the strands run parallel to each other (Gaultier et al. (1987) *Nucleic Acids Res* 15:6625–6641). The antisense nucleic acid molecule can also comprise a 2'-o-methylribonucleotide (Inoue et al. (1987) *Nucleic Acids Res* 15:6131–6148) or a chimeric RNA-DNA analogue (Inoue et al. (1987) *FEBS Lett* 215:327–330).

In still another embodiment, an antisense nucleic acid of the invention is a ribozyme. A ribozyme having specificity for a 47174-encoding nucleic acid can include one or more sequences complementary to the nucleotide sequence of a 47174 cDNA disclosed herein (i.e., SEQ ID NO:1 or SEQ ID NO:3), and a sequence having known catalytic sequence responsible for mRNA cleavage (see U.S. Pat. No. 5,093,246 or Haselhoff and Gerlach (1988) *Nature* 334:585–591). For example, a derivative of a Tetrahymena L-19 IVS RNA can be constructed in which the nucleotide sequence of the active site is complementary to the nucleotide sequence to be cleaved in a 47174-encoding mRNA. See, e.g., Cech et al. U.S. Pat. No. 4,987,071; and Cech et al. U.S. Pat. No. 5,116,742. Alternatively, 47174 mRNA can be used to select a catalytic RNA having a specific ribonuclease activity from a pool of RNA molecules. See, e.g., Bartel and Szostak (1993) *Science* 261:1411–1418.

47174 gene expression can be inhibited by targeting nucleotide sequences complementary to the regulatory region of the 47174 (e.g., the 47174 promoter and/or enhancers) to form triple helical structures that prevent transcription of the 47174 gene in target cells. See generally, Helene (1991) *Anticancer Drug Des* 6(6):569–84; Helene et al. (1992) *Ann NY Acad Sci* 660:27–36; and Maher (1992) *Bioassays* 14(12):807–15. The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or calorimetric.

A 47174 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup et al. (1996) *Bioorganic & Medicinal Chemistry* 4 (1): 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. *Proc Natl Acad Sci*. 93: 14670–675.

PNAs of 47174 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 47174 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup (1996) supra)); or as probes or primers for DNA sequencing or hybridization (Hyrup et al. (1996) supra; Perry-O'Keefe, supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc Natl Acad Sci USA* 86:6553–6556; Lemaitre et al. (1987) *Proc Natl Acad Sci USA* 84:648–652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) *Bio-Techniques* 6:958–976) or intercalating agents (See, e.g., Zon (1988) *Pharm Res* 5:539–549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 47174 nucleic acid of the invention, two complementary regions one having a fluorophore and one a quencher such that the molecular beacon is useful for quantitating the presence of the 47174 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 47174 Polypeptides

In another aspect, the invention features, an isolated 47174 protein, or fragment, e.g., a biologically active portion, for use as immunogens or antigens to raise or test (or more generally to bind) anti-47174 antibodies. 47174 protein can be isolated from cells or tissue sources using standard protein purification techniques. 47174 protein or fragments thereof can be produced by recombinant DNA techniques or synthesized chemically.

Polypeptides of the invention include those that arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a 47174 polypeptide has one or more of the following characteristics:

(i) it has the ability to transfer an activated sugar residue to an acceptor molecule;

(ii) it has a molecular weight, e.g., a deduced molecular weight, amino acid composition or other physical characteristic of a 47174 polypeptide, e.g., the polypeptide of SEQ ID NO:2;

(iii) it has an overall sequence similarity of at least 60%, more preferably at least 70, 80, 90, 95, 98, or 99%, with a polypeptide of SEQ ID NO:2;

(iv) it has a glycosyltransferase domain which preferably has an overall sequence similarity of about 70%, 80%, 90% or 95% with amino acid residues 154–336 of SEQ ID NO:2; or (v) it has at least 70%, preferably 80%, and most preferably 95% of the cysteines found amino acid sequence of the native protein.

In a preferred embodiment, the 47174 protein, or fragment thereof, includes at least two contiguous amino acids from the amino acid sequence of residues 1–170 or 437–603 of SEQ ID NO:2.

In a preferred embodiment the 47174 protein, or fragment thereof, differs from the corresponding sequence in SEQ ID NO:2. In one embodiment it differs by about 1, 2, 3, 4, 5, 6, 7, 8, 9, or more amino acids. In another it differs by at least one but less than 15, 10 or 5 amino acid residues. In another it differs from the corresponding sequence in SEQ ID NO:2 by at least 1%. In another it differs from the corresponding sequence in SEQ ID NO:2 by at least one residue but less than 20%, 15%, 10%, 5%, or 1% of the residues in it differ from the corresponding sequence in SEQ ID NO:2. If this comparison requires alignment the sequences should be aligned for maximum homology. "Looped" out sequences from deletions or insertions, or mismatches, are considered differences. The differences are, preferably, differences or changes at a non essential residue or a conservative substitution. In a preferred embodiment the differences are not in the glycosyltransferase domain (about amino acids 154 to 336 of SEQ ID NO:2). In another preferred embodiment one or more differences are in the glycosyltransferase domain (about amino acids 154 to 336 of SEQ ID NO:2).

Other embodiments include a protein that contains one or more changes in amino acid sequence, e.g., a change in an amino acid residue which is not essential for activity. Such 47174 proteins differ in amino acid sequence from SEQ ID NO:2, yet retain biological activity.

In one embodiment, the protein includes an amino acid sequence at least about 60%, 65%, 70%, 75%, 80%, 85%, 90%, 95%, 98%, 99%, or more homologous to SEQ ID NO:2.

A 47174 protein or fragment is provided which varies from the sequence of SEQ ID NO.2 in regions defined by amino acids about 1–153 or 337–603 by at least one but by less than 15, 10 or 5 amino acid residues in the protein or fragment but which does not differ from SEQ ID NO.2 in regions defined by amino acids about 154 to 336 of SEQ ID NO:2. If this comparison requires alignment the sequences should be aligned for maximum homology. "Looped" out sequences from deletions or insertions, or mismatches, are considered differences. In some embodiments the difference is at a non essential residue or is a conservative substitution, while in others the difference is at an essential residue or is a non conservative substitution.

In a preferred embodiment, a fragment differs by at least 1, 2, 3, 10, 20, or more amino acid residues encoded by a sequence present in WO00/58473, WO 01/53312, or WO 01/59063. Differences can include differing in length or sequence identity. For example, a fragment can: include one or more amino acid residues from SEQ ID NO:2 outside the region encoded by nucleotides 835–1633, 1011–2217, or 244–1389 of SEQ ID NO:1; not include all of the amino acid residues of a sequence present in WO00/58473, WO 01/53312, or WO 01/59063, e.g., can be one or more amino acid residues shorter (at one or both ends) than a sequence present in WO00/58473, WO 01/53312, or WO 01/59063; or can differ by one or more amino acid residues in the region of overlap.

In one embodiment, a biologically active portion of a 47174 protein includes a glycosyltransferase domain. Moreover, other biologically active portions, in which other regions of the protein are deleted, can be prepared by recombinant techniques and evaluated for one or more of the functional activities of a native 47174 protein.

In a preferred embodiment, the 47174 protein has an amino acid sequence shown in SEQ ID NO:2. In other embodiments, the 47174 protein is substantially identical to SEQ ID NO:2. In yet another embodiment, the 47174 protein is substantially identical to SEQ ID NO:2 and retains the functional activity of the protein of SEQ ID NO:2, as described in detail in the subsections above.

47174 Chimeric or Fusion Proteins

In another aspect, the invention provides 47174 chimeric or fusion proteins. As used herein, a 47174 "chimeric protein" or "fusion protein" includes a 47174 polypeptide linked to a non-47174 polypeptide. A "non-47174 polypeptide" refers to a polypeptide having an amino acid sequence corresponding to a protein which is not substantially homologous to the 47174 protein, e.g., a protein which is different from the 47174 protein and which is derived from the same or a different organism. The 47174 polypeptide of the fusion protein can correspond to all or a portion e.g., a fragment described herein of a 47174 amino acid sequence. In a preferred embodiment, a 47174 fusion protein includes at least one (or two) biologically active portion of a 47174 protein. The non-47174 polypeptide can be fused to the N-terminus or C-terminus of the 47174 polypeptide.

The fusion protein can include a moiety that has a high affinity for a ligand. For example, the fusion protein can be a GST-47174 fusion protein in which the 47174 sequences are fused to the C-terminus of the GST sequences. Such fusion proteins can facilitate the purification of recombinant 47174. Alternatively, the fusion protein can be a 47174 protein containing a heterologous signal sequence at its N-terminus. In certain host cells (e.g., mammalian host cells), expression and/or secretion of 47174 can be increased through use of a heterologous signal sequence.

Fusion proteins can include all or a part of a serum protein, e.g., an IgG constant region, or human serum albumin.

The 47174 fusion proteins of the invention can be incorporated into pharmaceutical compositions and administered to a subject in vivo. The 47174 fusion proteins can be used to affect the bioavailability of a 47174 substrate. 47174 fusion proteins may be useful therapeutically for the treatment of disorders caused by, for example, (i) aberrant modification or mutation of a gene encoding a 47174 protein; (ii) mis-regulation of the 47174 gene; and (iii) aberrant post-translational modification of a 47174 protein.

Moreover, the 47174-fusion proteins of the invention can be used as immunogens to produce anti-47174 antibodies in a subject, to purify 47174 ligands and in screening assays to identify molecules that inhibit the interaction of 47174 with a 47174 substrate.

Expression vectors are commercially available that already encode a fusion moiety (e.g., a GST polypeptide). A 47174-encoding nucleic acid can be cloned into such an expression vector such that the fusion moiety is linked in-frame to the 47174 protein.

Variants of 47174 Proteins

In another aspect, the invention also features a variant of a 47174 polypeptide, e.g., which functions as an agonist (mimetics) or as an antagonist. Variants of the 47174 proteins can be generated by mutagenesis, e.g., discrete point mutation, the insertion or deletion of sequences or the truncation of a 47174 protein. An agonist of the 47174 proteins can retain substantially the same, or a subset, of the biological activities of the naturally occurring form of a 47174 protein. An antagonist of a 47174 protein can inhibit one or more of the activities of the naturally occurring form of the 47174 protein by, for example, competitively modulating a 47174-mediated activity of a 47174 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 47174 protein.

Variants of a 47174 protein can be identified by screening combinatorial libraries of mutants, e.g., truncation mutants, of a 47174 protein for agonist or antagonist activity.

Libraries of fragments e.g., N-terminal, C-terminal, or internal fragments, of a 47174 protein coding sequence can be used to generate a variegated population of fragments for screening and subsequent selection of variants of a 47174 protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Recursive ensemble mutagenesis (REM), a new technique which enhances the frequency of functional mutants in the libraries, can be used in combination with the screening assays to identify 47174 variants (Arkin and Yourvan (1992) *Proc Natl Acad Sci USA* 89:7811–7815; Delgrave et al. (1993) *Protein Engineering* 6(3):327–331).

Cell based assays can be exploited to analyze a variegated 47174 library. For example, a library of expression vectors can be transfected into a cell line, e.g., a cell line, which ordinarily responds to 47174 in a substrate-dependent manner. The transfected cells are then contacted with 47174 and the effect of the expression of the mutant on signaling by the 47174 substrate can be detected, e.g., by measuring glycosyltransferase peptidase activity. Plasmid DNA can then be recovered from the cells which score for inhibition, or alternatively, potentiation of signaling by the 47174 substrate, and the individual clones further characterized.

In another aspect, the invention features a method of making a 47174 polypeptide, e.g., a peptide having a non-wild type activity, e.g., an antagonist, agonist, or super agonist of a naturally occurring 47174 polypeptide, e.g., a naturally occurring 47174 polypeptide. The method includes: altering the sequence of a 47174 polypeptide, e.g., altering the sequence by substitution or deletion of one or more residues of a non-conserved region, a domain or residue disclosed herein, and testing the altered polypeptide for the desired activity.

In another aspect, the invention features a method of making a fragment or analog of a 47174 polypeptide a biological activity of a naturally occurring 47174 polypeptide. The method includes: altering the sequence, e.g., by substitution or deletion of one or more residues, of a 47174 polypeptide, e.g., altering the sequence of a non-conserved region, or a domain or residue described herein, and testing the altered polypeptide for the desired activity.

Anti-47174 Antibodies

In another aspect, the invention provides an anti-47174 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91–3242, and Chothia, C. et al. (1987) *J. Mol. Biol.* 196:901–917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-47174 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH—terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 47174 polypeptide or fragment thereof. Examples of antigen-binding fragments of the anti-47174 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544–546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423–426; and Huston et al. (1988) *Proc. Natl. Acad. Sci. USA* 85:5879–5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-47174 antibody can be a polyclonal or a monoclonal antibody. In other embodiments, the antibody can be recombinantly produced, e.g., produced by phage display or by combinatorial methods.

Phage display and combinatorial methods for generating anti-47174 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffiths et al. (1993) *EMBO J* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982, the contents of all of which are incorporated by reference herein).

In one embodiment, the anti-47174 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856–859; Green, L. L. et al. 1994 *Nature Genet.* 7:13–21; Morrison, S. L. et al. 1994 *Proc. Natl. Acad. Sci. USA* 81:6851–6855; Bruggeman et al. 1993 *Year Immunol* 7:33–40; Tuaillon et al. 1993 *PNAS* 90:3720–3724; Bruggeman et al. 1991 *Eur J Immunol* 21:1323–1326).

An anti-47174 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041–1043); Liu et al. (1987) *PNAS* 84:3439–3443; Liu et al., 1987, *J. Immunol.* 139:3521–3526; Sun et al. (1987) *PNAS* 84:214–218; Nishimura et al., 1987, *Canc. Res.* 47:999–1005; Wood et al. (1985) *Nature* 314:446–449; and Shaw et al., 1988, *J. Natl Cancer Inst.* 80:1553–1559).

A humanized or CDR-grafted antibody will have at least one or two but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 47174 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202–1207, by Oi et al., 1986, *BioTechniques* 4:214, and by Queen et al. U.S. Pat. Nos. 5,585,089, 5,693,761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 47174 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 Nature 321:552–525; Verhoeyan et al. 1988 Science 239:1534; Beidler et al. 1988 J. Immunol. 141:4053–4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12–16 of U.S. Pat. No. 5,585,089, the e.g., columns 12–16 of U.S. Pat. No. 5,585,089, the contents of which are hereby incorporated by reference. Other techniques for humanizing antibodies are described in Padlan et al. EP 519596 A1, published on Dec. 23, 1992.

A full-length 47174 protein or, antigenic peptide fragment of 47174 can be used as an immunogen or can be used to identify anti-47174 antibodies made with other immunogens, e.g., cells, membrane preparations, and the like. The antigenic peptide of 47174 should include at least 8 amino acid residues of the amino acid sequence shown in SEQ ID NO:2 and encompasses an epitope of 47174. Preferably, the antigenic peptide includes at least 10 amino acid residues, more preferably at least 15 amino acid residues, even more preferably at least 20 amino acid residues, and most preferably at least 30 amino acid residues.

Fragments of 47174 which include residues about 151–175 of SEQ ID NO:2 can be used to make, e.g., used as immunogens or used to characterize the specificity of an antibody, antibodies against hydrophilic regions of the 47174 protein. Similarly, a fragment of 47174 which includes residues about 101–135 of SEQ ID NO:2 can be used to make an antibody against a hydrophobic region of the 47174 protein; a fragment of 47174 which include residues about 154–336 of SEQ ID NO:2, or a portion thereof (e.g., amino acids 154–174, 174–200, 200–220, 220–250, 250–275, 275–300, or 300–336 of SEQ ID NO:2), about can be used to make an antibody against the glycosyltransferase region of the 47174 protein.

Antibodies reactive with, or specific for, any of these regions, or other regions or domains described herein are provided.

Preferred epitopes encompassed by the antigenic peptide are regions of 47174 are located on the surface of the protein, e.g., hydrophilic regions, as well as regions with high antigenicity. For example, an Emini surface probability analysis of the human 47174 protein sequence can be used to indicate the regions that have a particularly high probability of being localized to the surface of the 47174 protein and are thus likely to constitute surface residues useful for targeting antibody production.

In a preferred embodiment the antibody binds an epitope on any domain or region on 47174 proteins described herein.

Chimeric, humanized, but most preferably, completely human antibodies are desirable for applications which include repeated administration, e.g., therapeutic treatment (and some diagnostic applications) of human patients.

The anti-47174 antibody can be a single chain antibody. A single-chain antibody (scFV) may be engineered (see, for example, Colcher et al. (1999) Ann N Y Acad Sci 880:263–80; and (1996) Reiter Clin Cancer Res 2:245–52). The single chain antibody can be dimerized or multimerized to generate multivalent antibodies having specificities for different epitopes of the same target 47174 protein.

In a preferred embodiment the antibody has effector function and/or can fix complement. In other embodiments the antibody does not recruit effector cells; or fix complement.

In a preferred embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

An anti-47174 antibody (e.g., monoclonal antibody) can be used to isolate 47174 by standard techniques, such as affinity chromatography or immunoprecipitation. Moreover, an anti-47174 antibody can be used to detect 47174 protein (e.g., in a cellular lysate or cell supernatant) in order to evaluate the abundance and pattern of expression of the protein. Anti-47174 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

The invention also includes a nucleic acid that encodes an anti-47174 antibody, e.g., an anti-47174 antibody described herein. Also included are vectors which include the nucleic acid and cells transformed with the nucleic acid, particularly cells that are useful for producing an antibody, e.g., mammalian cells, e.g. CHO or lymphatic cells.

The invention also includes cell lines, e.g., hybridomas, which make an anti-47174 antibody, e.g., and antibody described herein, and method of using said cells to make a 47174 antibody.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 47174 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 47174 proteins, mutant forms of 47174 proteins, fusion proteins, and the like).

The recombinant expression vectors of the invention can be designed for expression of 47174 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, Gene Expression Technology: *Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 47174 activity assays, (e.g., direct assays or competitive assays described in detail below), or to generate antibodies specific for 47174 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., Gene Expression Technology: *Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res* 20:2111–2118). Such alteration of nucleic acid sequences of the invention can be carried out by standard DNA synthesis techniques.

The 47174 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev* 1:268–277), lymphoid-specific promoters (Calame and Eaton (1988) *Adv Immunol* 43:235–275), in particular promoters of T cell receptors (Winoto and Baltimore (1989) *EMBO J* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc Natl Acad Sci USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example, the murine hox promoters (Kessel and Gruss (1990) *Science* 249:374–379) and the alpha-fetoprotein promoter (Campes and Tilghman (1989) *Genes Dev* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub et al. (1986) Antisense RNA as a molecular tool for genetic analysis, Reviews—Trends in Genetics, Vol. 1(1).

Another aspect the invention provides a host cell which includes a nucleic acid molecule described herein, e.g., a 47174 nucleic acid molecule within a recombinant expression vector or a 47174 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 47174 protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 47174 protein. Accordingly, the invention further provides methods for producing a 47174 protein using the host cells of the invention. In one embodiment, the method includes culturing the host cell of the invention (into which a recombinant expression vector encoding a 47174 protein has been introduced) in a suitable medium such that a 47174 protein is produced. In another embodiment, the method further includes isolating a 47174 protein from the medium or the host cell.

In another aspect, the invention features, a cell or purified preparation of cells which include a 47174 transgene, or which otherwise misexpress 47174. The cell preparation can consist of human or non human cells, e.g., rodent cells, e.g., mouse or rat cells, rabbit cells, or pig cells. In preferred embodiments, the cell or cells include a 47174 transgene, e.g., a heterologous form of a 47174, e.g., a gene derived from humans (in the case of a non-human cell). The 47174 transgene can be misexpressed, e.g., overexpressed or underexpressed. In other preferred embodiments, the cell or cells include a gene which misexpress an endogenous 47174, e.g., a gene the expression of which is disrupted, e.g., a knockout. Such cells can serve as a model for studying disorders which are related to mutated or misexpressed 47174 alleles or for use in drug screening.

In another aspect, the invention features, a human cell, e.g., a CNS cell or a kidney cell, transformed with nucleic acid that encodes a subject 47174 polypeptide.

Also provided are cells, preferably human cells, e.g., human hematopoietic or fibroblast cells, in which an endogenous 47174 is under the control of a regulatory sequence that does not normally control the expression of the endogenous 47174 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 47174 gene. For example, an endogenous 47174 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published May 16, 1991.

Transgenic Animals

The invention provides non-human transgenic animals. Such animals are useful for studying the function and/or activity of a 47174 protein and for identifying and/or evaluating modulators of 47174 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 47174 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 47174 protein to particular cells. A transgenic founder animal can be identified based upon the presence of a 47174 transgene in its genome and/or expression of 47174 mRNA in tissues or cells of the animals. A transgenic founder animal can then be used to breed additional animals carrying the transgene. Moreover, transgenic animals carrying a transgene encoding a 47174 protein can further be bred to other transgenic animals carrying other transgenes.

47174 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 47174 protein (e.g., via a recombinant expression vector in a host cell in gene therapy applications), to detect a 47174 mRNA (e.g., in a biological sample) or a genetic alteration in a 47174 gene, and to modulate 47174 activity, as described further below. The 47174 proteins can be used to treat disorders characterized by insufficient or excessive production of a 47174 substrate or production of 47174 inhibitors. In addition, the 47174 proteins can be used to screen for naturally occurring 47174 substrates, to screen for drugs or compounds which modulate 47174 activity, as well as to treat disorders characterized by insufficient or excessive production of 47174 protein or production of 47174 protein forms which have decreased, aberrant or unwanted activity compared to 47174 wild type protein (e.g., pain or pain related disorders). Moreover, the anti-47174 antibodies of the invention can be used to detect and isolate 47174 proteins, regulate the bioavailability of 47174 proteins, and modulate 47174 activity.

A method of evaluating a compound for the ability to interact with, e.g., bind, a subject 47174 polypeptide is provided. The method includes: contacting the compound with the subject 47174 polypeptide; and evaluating ability of the compound to interact with, e.g., to bind, form a complex with, or act as a substrate for, or of, the subject 47174 polypeptide. This method can be performed in vitro, e.g., in a cell free system, or in vivo, e.g., in a two-hybrid interaction trap assay. This method can be used to identify naturally occurring molecules which interact with subject 47174 polypeptide. It can also be used to find natural or synthetic inhibitors of subject 47174 polypeptide. Screening methods are discussed in more detail below.

Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 47174 proteins, have a stimulatory or inhibitory effect on, for example, 47174 expression or 47174 activity, or have a stimulatory or inhibitory effect on, for example, the expression or activity of a 47174 substrate. Compounds thus identified can be used to modulate the activity of target gene products (e.g., 47174 genes) in a therapeutic protocol, to elaborate the biological function of the target gene product, or to identify compounds that disrupt normal target gene interactions.

In one embodiment, the invention provides assays for screening candidate or test compounds that are substrates of a 47174 protein or polypeptide or a biologically active portion thereof. In another embodiment, the invention provides assays for screening candidate or test compounds that bind to or modulate the activity of a 47174 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al. (1994) *J Med Chem* 37: 2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des* 12:145).

Examples of methods for the synthesis of molecular libraries can be found in the art, for example in: DeWitt et al. (1993) *Proc Natl Acad Sci USA* 90:6909; Erb et al. (1994) *Proc Natl Acad Sci USA* 91:11422; Zuckermann et al. (1994). *J. Med. Chem.* 37:2678; Cho et al. (1993) *Science* 261:1303; Carrell et al. (1994) *Angew Chem Int Ed Engl.* 33:2059; Carell et al. (1994) *Angew Chem Int Ed Engl* 33:2061; and in Gallop et al. (1994) *J Med Chem* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc Natl Acad Sci USA* 87:6378–6382; Felici (1991) *J Mol Biol* 222:301–310; Ladner, supra.

In one embodiment, an assay is a cell-based assay in which a cell which expresses a 47174 protein or biologically active portion thereof is contacted with a test compound, and the ability of the test compound to modulate 47174 activity is determined. Determining the ability of the test compound to modulate 47174 activity can be accomplished by monitoring, for example, glycosyltransferase activity, e.g., zinc binding activity or hydrolysis of a peptide substrate, e.g., enkephalin cleavage activity. The cell, for example, can be of mammalian origin, e.g., human.

The ability of the test compound to modulate 47174 binding to a compound, e.g., a 47174 substrate, or to bind to 47174 can also be evaluated. This can be accomplished, for example, by coupling the compound, e.g., the substrate, with a radioisotope or enzymatic label such that binding of the compound, e.g., the substrate, to 47174 can be determined by detecting the labeled compound, e.g., substrate, in a complex. Alternatively, 47174 could be coupled with a radioisotope or enzymatic label to monitor the ability of a test compound to modulate 47174 binding to a 47174 substrate in a complex. For example, compounds (e.g., 47174 substrates) can be labeled with $^{125}I$, $^{35}I$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 47174 substrate) to interact with 47174 with or without the labeling of any of the interactants can be evaluated. For example, a microphysiometer can be used to detect the interaction of a compound with 47174 without the labeling of either the compound or the 47174. McConnell et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 47174.

In yet another embodiment, a cell-free assay is provided in which a 47174 protein or biologically active portion thereof is contacted with a test compound and the ability of the test compound to bind to the 47174 protein or biologically active portion thereof is evaluated. Preferred biologically active portions of the 47174 proteins to be used in assays of the present invention include fragments that participate in interactions with non-47174 molecules, e.g., fragments with high surface probability scores.

Soluble and/or membrane-bound forms of isolated proteins (e.g., 47174 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 47174 protein to bind to a target molecule or substrate can be accomplished using real-time Biomolecular Interaction Analysis (BIA) (see, e.g., Sjolander and Urbaniczky (1991) *Anal Chem* 63:2338–2345 and Szabo et al. (1995) *Curr Opin Struct Biol* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 47174, an anti-47174 antibody or its target molecule to facilitate separation of complexed from uncomplexed forms of one or both of the proteins, as well as to accommodate automation of the assay. Binding of a test compound to a 47174 protein, or interaction of a 47174 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/47174 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 47174 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 47174 binding or activity determined using standard techniques.

Other techniques for immobilizing either a 47174 protein or a target molecule on matrices include using conjugation of biotin and streptavidin. Biotinylated 47174 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 47174 protein or target molecules but which do not interfere with binding of the 47174 protein to its target molecule. Such antibodies can be derivatized to the wells of the plate, and unbound target or 47174 protein trapped in the wells by antibody conjugation. Methods for detecting such complexes, in addition to those described above for the GST-immobilized complexes, include immunodetection of complexes using antibodies reactive with the 47174 protein or target molecule, as well as enzyme-linked assays which rely on detecting an enzymatic activity associated with the 47174 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas and Minton (1993) *Trends Biochem Sci* 18(8):284–7); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel, F. et al., eds. Current Protocols in Molecular Biology 1999, J. Wiley: New York). Such resins and chromatographic techniques are known to one skilled in the art (see, e.g., Heegaard (1998) *J Mol Recognit* 11(1–6):141–8; Hage and Tweed (1997) *J Chromatogr B Biomed Sci Appl* 699(1–2):499–525). Further, fluorescence energy transfer may also be conveniently utilized, as described herein, to detect binding without further purification of the complex from solution.

In a preferred embodiment, the assay includes contacting the 47174 protein or biologically active portion thereof with a known compound which binds 47174 to form an assay mixture, contacting the assay mixture with a test compound, and determining the ability of the test compound to interact with a 47174 protein, wherein determining the ability of the test compound to interact with a 47174 protein includes determining the ability of the test compound to preferentially bind to 47174 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 47174 genes herein identified. In an alternative embodiment, the invention provides methods for determining the ability of the test compound to modulate the activity of a 47174 protein through modulation of the activity of a downstream effector of a 47174 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 47174 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J Biol Chem* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 47174 ("47174-binding proteins" or "47174-bp") and are involved in 47174 activity. Such 47174-bps can be activators or inhibitors of signals by the 47174 proteins or 47174 targets as, for example, downstream elements of a 47174-mediated signaling pathway.

The two-hybrid system is based on the modular nature of most transcription factors, which consist of separable DNA-binding and activation domains. Briefly, the assay utilizes two different DNA constructs. In one construct, the gene that codes for a 47174 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively 47174 protein can be the fused to the activator domain.) If the "bait" and the "prey" proteins are able to interact, in vivo, forming a 47174-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 47174 protein.

In another embodiment, modulators of 47174 expression are identified. For example, a cell or cell free mixture is contacted with a candidate compound and the expression of 47174 mRNA or protein evaluated relative to the level of expression of 47174 mRNA or protein in the absence of the candidate compound. When expression of 47174 mRNA or protein is greater in the presence of the candidate compound than in its absence, the candidate compound is identified as a stimulator of 47174 mRNA or protein expression. Alternatively, when expression of 47174 mRNA or protein is less (statistically significantly less) in the presence of the candidate compound than in its absence, the candidate compound is identified as an inhibitor of 47174 mRNA or protein expression. The level of 47174 mRNA or protein expression can be determined by methods described herein for detecting 47174 mRNA or protein.

In another aspect, the invention pertains to a combination of two or more of the assays described herein. For example, a modulating agent can be identified using a cell-based or a cell free assay, e.g., a peptidase assay, and the ability of the agent to modulate the activity of a 47174 protein can be confirmed in vivo, e.g., in an animal such as an animal model for pain response, e.g., an arthritic rodent, a CCI rodent model for neuropathic pain, or a rodent with induced unilateral inflammatory pain by intraplantar injection of Freund's complete adjuvant.

This invention further pertains to novel agents identified by the above-described screening assays. Accordingly, it is within the scope of this invention to further use an agent identified as described herein (e.g., a 47174 modulating agent, an antisense 47174 nucleic acid molecule, a 47174-specific antibody, or a 47174-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 47174 with a disease; (ii) identify an individual from a minute biological sample (tissue typing); and (iii) aid in forensic identification of a biological sample. These applications are described in the subsections below.

Chromosome Mapping

The 47174 nucleotide sequences or portions thereof can be used to map the location of the 47174 genes on a chromosome. This process is called chromosome mapping. Chromosome mapping is useful in correlating the 47174 sequences with genes associated with disease.

Briefly, 47174 genes can be mapped to chromosomes by preparing PCR primers (preferably 15–25 bp in length) from the 47174 nucleotide sequences. These primers can then be used for PCR screening of somatic cell hybrids containing individual human chromosomes. Only those hybrids containing the human gene corresponding to the 47174 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio et al. (1983) *Science* 220:919–924).

Other mapping strategies e.g., in situ hybridization (described in Fan et al. (1990) *Proc Natl Acad Sci USA* 87:6223–27), pre-screening with labeled flow-sorted chromosomes, and pre-selection by hybridization to chromosome specific cDNA libraries can be used to map 47174 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland et al. (1987) *Nature* 325:783–787.

Moreover, differences in the DNA sequences between individuals affected and unaffected with a disease associated with the 47174 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 47174 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 47174 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from 47174 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 47174 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 (e.g., fragments derived from the noncoding regions of SEQ ID NO:1 having a length of at least 20 bases, preferably at least 30 bases) are particularly appropriate for this use.

The 47174 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 47174 probes can be used to identify tissue by species and/or by organ type.

In a similar fashion, these reagents, e.g., 47174 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 47174.

Such disorders include, e.g., disorders associated with the misexpression of 47174 gene: pain, pain related disorders.

The method includes one or more of the following:

detecting, in a tissue of the subject, the presence or absence of a mutation which affects the expression of the 47174 gene, or detecting the presence or absence of a mutation in a region which controls the expression of the gene, e.g., a mutation in the 5' control region;

detecting, in a tissue of the subject, the presence or absence of a mutation which alters the structure of the 47174 gene;

detecting, in a tissue of the subject, the misexpression of the 47174 gene, at the mRNA level, e.g., detecting a non-wild type level of a mRNA;

detecting, in a tissue of the subject, the misexpression of the gene, at the protein level, e.g., detecting a non-wild type level of a 47174 polypeptide.

In preferred embodiments the method includes: ascertaining the existence of at least one of: a deletion of one or more nucleotides from the 47174 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, or naturally occurring mutants thereof or 5' or 3' flanking sequences naturally associated with the 47174 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 47174 gene; the presence of a non-wild type splicing pattern of a messenger RNA transcript of the gene; or a non-wild type level of 47174.

Methods of the invention can be used prenatally or to determine if a subject's offspring will be at risk for a disorder.

In preferred embodiments the method includes determining the structure of a 47174 gene, an abnormal structure being indicative of risk for the disorder.

In preferred embodiments the method includes contacting a sample form the subject with an antibody to the 47174 protein or a nucleic acid, which hybridizes specifically with the gene. There and other embodiments are discussed below.

Diagnostic and Prognostic Assays

Diagnostic and prognostic assays of the invention include method for assessing the expression level of 47174 molecules and for identifying variations and mutations in the sequence of 47174 molecules.

Expression Monitoring and Profiling.

The presence, level, or absence of 47174 protein or nucleic acid in a biological sample can be evaluated by obtaining a biological sample from a test subject and contacting the biological sample with a compound or an agent capable of detecting 47174 protein or nucleic acid (e.g., mRNA, genomic DNA) that encodes 47174 protein such that the presence of 47174 protein or nucleic acid is detected in the biological sample. The term "biological sample" includes tissues, cells and biological fluids isolated from a subject, as well as tissues, cells and fluids present within a subject. A preferred biological sample is serum. The level of expression of the 47174 gene can be measured in a number of ways, including, but not limited to: measuring the mRNA encoded by the 47174 genes; measuring the amount of protein encoded by the 47174 genes; or measuring the activity of the protein encoded by the 47174 genes.

The level of mRNA corresponding to the 47174 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 47174 nucleic acid, such as the nucleic acid of SEQ ID NO:1, or a portion thereof, such as an oligonucleotide of at least 7, 15, 30, 50, 100, 250 or 500 nucleotides in length and sufficient to specifically hybridize under stringent conditions to 47174 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 47174 genes.

The level of mRNA in a sample that is encoded by one of 47174 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189–193), self sustained sequence replication (Guatelli et al., (1990) *Proc. Natl. Acad. Sci. USA* 87:1874–1878), transcriptional amplification system (Kwoh et al., (1989) *Proc. Natl. Acad. Sci. USA* 86:1173–1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 47174 gene being analyzed.

In another embodiment, the methods further contacting a control sample with a compound or agent capable of detecting 47174 mRNA, or genomic DNA, and comparing the presence of 47174 mRNA or genomic DNA in the control sample with the presence of 47174 mRNA or genomic DNA in the test sample. In still another embodiment, serial analysis of gene expression, as described in U.S. Pat. No. 5,695,937, is used to detect 47174 transcript levels.

A variety of methods can be used to determine the level of protein encoded by 47174. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 47174 protein in a biological sample in vitro as well as in vivo. In vitro techniques for detection of 47174 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 47174 protein include introducing into a subject a labeled anti-47174 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-47174 antibody positioned on an antibody array (as described below). The sample can be detected, e.g., with avidin coupled to a fluorescent label.

In another embodiment, the methods further include contacting the control sample with a compound or agent capable of detecting 47174 protein, and comparing the presence of 47174 protein in the control sample with the presence of 47174 protein in the test sample.

The invention also includes kits for detecting the presence of 47174 in a biological sample. For example, the kit can include a compound or agent capable of detecting 47174 protein or mRNA in a biological sample; and a standard. The compound or agent can be packaged in a suitable container. The kit can further comprise instructions for using the kit to detect 47174 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 47174 expression or activity. As used herein, the term "unwanted" includes an unwanted phenomenon involved in a biological response such as oligodendrocyte development, myelin formation, pain or deregulated cell proliferation.

In one embodiment, a disease or disorder associated with aberrant or unwanted 47174 expression or activity is identified. A test sample is obtained from a subject and 47174 protein or nucleic acid (e.g., mRNA or genomic DNA) is evaluated, wherein the level, e.g., the presence or absence, of 47174 protein or nucleic acid is diagnostic for a subject having or at risk of developing a disease or disorder associated with aberrant or unwanted 47174 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 47174 expression or activity. For example, such methods can be used to determine whether a subject can be effectively treated with an agent for a disorder as described herein.

In another aspect, the invention features a computer medium having a plurality of digitally encoded data records. Each data record includes a value representing the level of expression of 47174 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 47174 (e.g., other genes associated with a 47174-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 47174 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a DISORDERA disorder in a subject wherein an increase in 47174 expression is an indication that the subject has or is disposed to having a disorder as described herein. The method can be used to monitor a treatment for the disorder in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 47174 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 47174 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 47174 expression.

Arrays and Uses Thereof

In another aspect, the invention features an array that includes a substrate having a plurality of addresses. At least one address of the plurality includes a capture probe that binds specifically to a 47174 molecule (e.g., a 47174 nucleic acid or a 47174 polypeptide). The array can have a density of at least than 10, 50, 100, 200, 500, 1,000, 2,000, or 10,000 or more addresses/cm², and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 47174 nucleic acid, e.g., the sense or anti-sense strand. In one preferred embodiment, a subset of addresses of the plurality of addresses has a nucleic acid capture probe for 47174. Each address of the subset can include a capture probe that hybridizes to a different region of a 47174 nucleic acid. In another preferred embodiment, addresses of the subset include a capture probe for a 47174 nucleic acid. Each address of the subset is unique, overlapping, and complementary to a different variant of 47174 (e.g., an allelic variant, or all possible hypothetical variants). The array can be used to sequence 47174 by hybridization (see, e.g., U.S. Pat. No. 5,695,940).

An array can be generated by various methods, e.g., by photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 47174 polypeptide or fragment thereof. The polypeptide can be a naturally-occurring interaction partner of 47174 polypeptide. Preferably, the polypeptide is an antibody, e.g., an antibody described herein (see "Anti-47174 Antibodies," above), such as a monoclonal antibody or a single-chain antibody.

In another aspect, the invention features a method of analyzing the expression of 47174. The method includes providing an array as described above; contacting the array with a sample and detecting binding of a 47174-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 47174. If a sufficient number of diverse samples is analyzed, clustering (e.g., hierarchical clustering, k-means clustering, Bayesian clustering and the like) can be used to identify other genes which are co-regulated with 47174. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 47174 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 47174-associated disease or disorder; and processes, such as a cellular transformation associated with a 47174-associated disease or disorder. The method can also evaluate the treatment and/or progression of a 47174-associated disease or disorder.

The array is also useful for ascertaining differential expression patterns of one or more genes in normal and abnormal cells. This provides a battery of genes (e.g., including 47174) that could serve as a molecular target for diagnosis or therapeutic intervention.

In another aspect, the invention features an array having a plurality of addresses. Each address of the plurality includes a unique polypeptide. At least one address of the plurality has disposed thereon a 47174 polypeptide or fragment thereof. Methods of producing polypeptide arrays are described in the art, e.g., in De Wildt et al. (2000). *Nature Biotech*. 18, 989–994; Lueking et al. (1999). *Anal. Biochem*. 270, 103–111; Ge, H. (2000). *Nucleic Acids Res*. 28, e3, I–VII; MacBeath, G., and Schreiber, S. L. (2000). *Science* 289, 1760–1763; and WO 99/51773A1. In a preferred embodiment, each addresses of the plurality has disposed thereon a polypeptide at least 60, 70, 80,85, 90, 95 or 99% identical to a 47174 polypeptide or fragment thereof. For example, multiple variants of a 47174 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 47174 binding compound, e.g., an antibody in a sample from a subject with specificity for a 47174 polypeptide or the presence of a 47174-binding protein or ligand.

The array is also useful for ascertaining the effect of the expression of a gene on the expression of other genes in the same cell or in different cells (e.g., ascertaining the effect of 47174 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 47174 or from a cell or subject in which a 47174 mediated response has been elicited, e.g., by contact of the cell with 47174 nucleic acid or protein, or administration to the cell or subject 47174 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 47174 (or does not express as highly as in the case of the 47174 positive plurality of capture probes) or from a cell or subject which in which a 47174 mediated response has not been elicited (or has been elicited to a lesser extent than in the first sample); contacting the array with one or more inquiry probes (which is preferably other than a 47174 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 47174 or from a cell or subject in which a 47174-mediated response has been elicited, e.g., by contact of the cell with 47174 nucleic acid or protein, or administration to the cell or subject 47174 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 47174 (or does not express as highly as in the case of the 47174 positive plurality of capture probes) or from a cell or subject which in which a 47174 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 47174, e.g., analyzing structure, function, or relatedness to other nucleic acid or amino acid sequences. The method includes: providing a 47174 nucleic acid or amino acid sequence; comparing the 47174 sequence with one or more preferably a plurality of sequences from a collection of sequences, e.g., a nucleic acid or protein sequence database; to thereby analyze 47174.

Detection of Variations or Mutations

The methods of the invention can also be used to detect genetic alterations in a 47174 gene, thereby determining if a subject with the altered gene is at risk for a disorder characterized by misregulation in 47174 protein activity or nucleic acid expression, such as a disorder as described herein. In preferred embodiments, the methods include detecting, in a sample from the subject, the presence or absence of a genetic alteration characterized by at least one of an alteration affecting the integrity of a gene encoding a 47174-protein, or the mis-expression of the 47174 gene. For example, such genetic alterations can be detected by ascertaining the existence of at least one of 1) a deletion of one or more nucleotides from a 47174 gene; 2) an addition of one or more nucleotides to a 47174 gene; 3) a substitution of one or more nucleotides of a 47174 gene, 4) a chromosomal rearrangement of a 47174 gene; 5) an alteration in the level of a messenger RNA transcript of a 47174 gene, 6) aberrant modification of a 47174 gene, such as of the methylation pattern of the genomic DNA, 7) the presence of a non-wild type splicing pattern of a messenger RNA transcript of a 47174 gene, 8) a non-wild type level of a 47174-protein, 9) allelic loss of a 47174 gene, and 10) inappropriate post-translational modification of a 47174-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 47174-gene. This method can include the steps of collecting a sample of cells from a subject, isolating nucleic acid (e.g., genomic, mRNA or both) from the sample, contacting the nucleic acid sample with one or more primers which specifically hybridize to a 47174 gene under conditions such that hybridization and amplification of the 47174-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 47174 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 47174 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 47174 nucleic acid or a putative variant (e.g., allelic variant) thereof. A probe can have one or more mismatches to a region of a 47174 nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in 47174 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 47174 gene and detect mutations by comparing the sequence of the sample 47174 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 47174 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol*. 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 47174 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in 47174 genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat. Res*. 285:125–144; and Hayashi (1992) *Genet. Anal. Tech. Appl*. 9:73–79). Single-stranded DNA fragments of sample and control 47174 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol*. 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res*. 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 47174 nucleic acid.

In a preferred embodiment the set includes a first and a second oligonucleotide. The first and second oligonucleotide can hybridize to the same or to different locations of SEQ ID NO:1 or 3 or the complement of SEQ ID NO:1 or 3. Different locations can be different but overlapping or or nonoverlapping on the same strand. The first and second oligonucleotide can hybridize to sites on the same or on different strands.

The set can be useful, e.g., for identifying SNP's, or identifying specific alleles of 47174. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 47174 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 47174 gene.

Use of 47174 Molecules as Surrogate Markers

The 47174 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 47174 molecules of the invention may be detected, and may be correlated with one or more biological states in vivo. For example, the 47174 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The 47174 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 47174 marker) transcription or expression, the amplified marker may be in a quantity which is more readily detectable than the drug itself. Also, the marker may be more easily detected due to the nature of the marker itself; for example, using the methods described herein, anti-47174 antibodies may be employed in an immune-based detection system for a 47174 protein marker, or 47174-specific radiolabeled probes may be used to detect a 47174 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am, J Health-Syst. Pharm.* 56 Suppl. 3: S16–S20.

The 47174 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 47174 protein or RNA) for specific tumor markers in a subject, a drug or course of treatment may be selected that is optimized for the treatment of the specific tumor likely to be present in the subject. Similarly, the presence or absence of a specific sequence mutation in 47174 DNA may correlate 47174 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-47174 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e.,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208, 020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors. Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc Natl Acad Sci USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 47174 expression or activity. "Treatment" or "treating a subject" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype," or "drug response genotype"). Thus, another aspect of the invention provides methods for tailoring an individual's prophylactic or therapeutic treatment with either the 47174 molecules of the present invention or 47174 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 47174 expression or activity, by administering to the subject a 47174 or an agent which modulates 47174 expression or at least one 47174 activity. Subjects at risk for a disease which is caused or contributed to by aberrant or unwanted 47174 expression or activity can be identified by, for example, any or a combination of diagnostic or prognostic assays as described herein. Administration of a prophylactic agent can occur prior to the manifestation of symptoms characteristic of the 47174 aberrance, such that a disease or disorder is prevented or, alternatively, delayed in its progression. Depending on the type of 47174 aberrance, for example, a 47174 agonist or 47174 antagonist agent can be used for treating the subject. The appropriate agent can be determined based on screening assays described herein.

As the 47174 mRNA is expressed in brain cortex and hypothalamus, the molecules of the invention can be used to treat, prevent, and/or diagnose disorders involving activities of CNS, as described above.

It is possible that some 47174 disorders can be caused, at least in part, by an abnormal level of gene product, or by the presence of a gene product exhibiting abnormal activity. As such, the reduction in the level and/or activity of such gene products would bring about the amelioration of disorder symptoms, for example, in neurological, e.g., CNS-related or pain-related disorders.

As discussed, successful treatment of 47174 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 47174 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')2 and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 47174 expression is through the use of aptamer molecules specific for 47174 protein. Aptamers are nucleic acid molecules having a tertiary structure which permits them to specifically bind to protein ligands (see, e.g., Osborne et al. (1997) *Curr Opin Chem Biol* 1(1): 5–9; and Patel (1997) *Curr Opin Chem Biol* 1(1):32–46). Since nucleic acid molecules may in many cases be more conveniently introduced into target cells than therapeutic protein molecules may be, aptamers offer a method by which 47174 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 47174 disorders. For a description of antibodies, see the Antibody section above.

In circumstances wherein injection of an animal or a human subject with a 47174 protein or epitope for stimulating antibody production is harmful to the subject, it is possible to generate an immune response against 47174 through the use of anti-idiotypic antibodies (see, for example, Herlyn (1999) *Ann Med* 31(1):66–78; and Bhattacharya-Chatterjee and Foon (1998) *Cancer Treat Res* 94:51–68). If an anti-idiotypic antibody is introduced into a mammal or human subject, it should stimulate the production of anti-anti-idiotypic antibodies, which should be specific to the 47174 protein. Vaccines directed to a disease characterized by 47174 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc Natl Acad Sci USA* 90:7889–7893).

The identified compounds that inhibit target gene expression, synthesis and/or activity can be administered to a patient at therapeutically effective doses to prevent, treat or ameliorate 47174 disorders, e.g., to control CNS disorders, e.g., pain or pain related disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 47174 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell et al (1996) *Current Opinion in Biotechnology* 7:89–94 and in Shea (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis et al (1993) *Nature* 361:645–647. Through the use of isotope-labeling, the "free" concentration of compound which modulates the expression or activity of 47174 can be readily monitored and used in calculations of IC50.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual IC50. An rudimentary example of such a "biosensor" is discussed in Kriz et al. (1995) *Analytical Chemistry* 67:2142–2144.

Another aspect of the invention pertains to methods of modulating 47174 expression or activity for therapeutic purposes. Accordingly, in an exemplary embodiment, the modulatory method of the invention involves contacting a cell with a 47174 or agent that modulates one or more of the activities of 47174 protein activity associated with the cell. An agent that modulates 47174 protein activity can be an agent as described herein, such as a nucleic acid or a protein, a naturally-occurring target molecule of a 47174 protein (e.g., a 47174 substrate or receptor), a 47174 antibody, a 47174 agonist or antagonist, a peptidomimetic of a 47174 agonist or antagonist, or other small molecule.

In one embodiment, the agent stimulates one or 47174 activities. Examples of such stimulatory agents include active 47174 protein and a nucleic acid molecule encoding 47174. In another embodiment, the agent inhibits one or more 47174 activities. Examples of such inhibitory agents include antisense 47174 nucleic acid molecules, anti 47174 antibodies, and 47174 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 47174 protein or nucleic acid molecule. In one embodiment, the method involves administering an agent (e.g., an agent identified by a screening assay described herein), or combination of agents that modulates (e.g., up regulates or down regulates) 47174 expression or activity. In another embodiment, the method involves administering a 47174 protein or nucleic acid molecule as therapy to compensate for reduced, aberrant, or unwanted 47174 expression or activity.

Stimulation of 47174 activity is desirable in situations in which 47174 is abnormally downregulated and/or in which increased 47174 activity is likely to have a beneficial effect. For example, stimulation of 47174 activity is desirable in situations in which a 47174 is downregulated and/or in which increased 47174 activity is likely to have a beneficial effect. Likewise, inhibition of 47174 activity is desirable in situations in which 47174 is abnormally upregulated and/or in which decreased 47174 activity is likely to have a beneficial effect.

Pharmacogenomics

The 47174 molecules of the present invention, as well as agents, or modulators which have a stimulatory or inhibitory effect on 47174 activity (e.g., 47174 gene expression) as identified by a screening assay described herein can be administered to individuals to treat (prophylactically or therapeutically) 47174 associated disorders (e.g., CNS, pain, pain related disorders) associated with aberrant or unwanted 47174 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 47174 molecule or 47174 modulator as well as tailoring the dosage and/or therapeutic regimen of treatment with a 47174 molecule or 47174 modulator.

Pharmacogenomics deals with clinically significant hereditary variations in the response to drugs due to altered drug disposition and abnormal action in affected persons. See, for example, Eichelbaum et al. (1996) *Clin Exp Pharmacol Physiol* 23(10–11):983–985 and Linder et al. (1997) *Clin Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a 47174 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 47174 molecule or 47174 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 47174 molecule or 47174 modulator, such as a modulator identified by one of the exemplary screening assays described herein.

The present invention further provides methods for identifying new agents, or combinations, that are based on identifying agents that modulate the activity of one or more of the gene products encoded by one or more of the 47174 genes of the present invention, wherein these products may be associated with resistance of the cells to a therapeutic agent. Specifically, the activity of the proteins encoded by the 47174 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 47174 protein can be applied in clinical trials. For example, the effectiveness of an agent determined by a screening assay as described herein to increase 47174 gene expression, protein levels, or upregulate 47174 activity, can be monitored in clinical trials of subjects exhibiting decreased 47174 gene expression, protein levels, or downregulated 47174 activity. Alternatively, the effectiveness of an agent determined by a screening assay to decrease 47174 gene expression, protein levels, or downregulate 47174 activity, can be monitored in clinical trials of subjects exhibiting increased 47174 gene expression, protein levels, or upregulated 47174 activity. In such clinical trials, the expression or activity of a 47174 gene, and preferably, other genes that have been implicated in, for example, a 47174-associated disorder can be used as a "read out" or markers of the phenotype of a particular cell.

47174 Informatics

The sequence of a 47174 molecule is provided in a variety of media to facilitate use thereof. A sequence can be provided as a manufacture, other than an isolated nucleic acid or amino acid molecule, which contains a 47174. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 47174 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 47174, e.g., analyzing structure, function, or relatedness to one or more other nucleic acid or amino acid sequences. The method includes: providing a 47174 nucleic acid or amino acid sequence; comparing the 47174 sequence with a second sequence, e.g., one or more preferably a plurality of sequences from a collection of sequences, e.g., a nucleic acid or protein sequence database to thereby analyze 47174. The method can be performed in a machine, e.g., a computer, or manually by a skilled artisan.

The method can include evaluating the sequence identity between a 47174 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 47174 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 47174 sequence, or record, in machine-readable form; comparing a second sequence to the 47174 sequence; thereby analyzing a sequence. Comparison can include comparing to sequences for sequence identity or determining if one sequence is included within the other, e.g., determining if the 47174 sequence includes a sequence being compared. In a preferred embodiment the 47174 or second sequence is stored on a first computer, e.g., at a first site and the comparison is performed, read, or recorded on a second computer, e.g., at a second site. E.g., the 47174 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 47174-associated disease or disorder or a pre-disposition to a 47174-associated disease or disorder, wherein the method comprises the steps of determining 47174 sequence information associated with the subject and based on the 47174 sequence information, determining whether the subject has a 47174-associated disease or disorder or a pre-disposition to a 47174-associated disease or disorder and/or recommending a particular treatment for the disease, disorder or pre-disease condition.

The invention further provides in an electronic system and/or in a network, a method for determining whether a subject has a 47174-associated disease or disorder or a pre-disposition to a disease associated with a 47174 wherein the method comprises the steps of determining 47174 sequence information associated with the subject, and based on the 47174 sequence information, determining whether the subject has a 47174-associated disease or disorder or a pre-disposition to a 47174-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 47174 sequence of the subject to the 47174 sequences in the database to thereby determine whether the subject as a 47174-associated disease or disorder, or a pre-disposition for such.

The present invention also provides in a network, a method for determining whether a subject has a 47174 associated disease or disorder or a pre-disposition to a 47174-associated disease or disorder associated with 47174, said method comprising the steps of receiving 47174 sequence information from the subject and/or information related thereto, receiving phenotypic information associated with the subject, acquiring information from the network corresponding to 47174 and/or corresponding to a 47174-associated disease or disorder (e.g., CNS or pain related disorders), and based on one or more of the phenotypic information, the 47174 information (e.g., sequence information and/or information related thereto), and the acquired information, determining whether the subject has a 47174-associated disease or disorder or a pre-disposition to a 47174-associated disease or disorder. The method may further comprise the step of recommending a particular treatment for the disease, disorder or pre-disease condition.

The present invention also provides a method for determining whether a subject has a 47174-associated disease or disorder or a pre-disposition to a 47174-associated disease or disorder, said method comprising the steps of receiving information related to 47174 (e.g., sequence information and/or information related thereto), receiving phenotypic information associated with the subject, acquiring information from the network related to 47174 and/or related to a 47174-associated disease or disorder, and based on one or more of the phenotypic information, the 47174 information, and the acquired information, determining whether the subject has a 47174-associated disease or disorder or a pre-disposition to a 47174-associated disease or disorder. The method may further comprise the step of recommending a particular treatment for the disease, disorder or pre-disease condition.

This invention is further illustrated by the following examples which should not be construed as limiting. The contents of all references, patents and published patent applications cited throughout this application are incorporated herein by reference.

EXAMPLES

Example 1

Identification and Characterization of Human 47174 cDNA

The human 47174 nucleic acid sequence is recited as follows:

```
GCGCCGCCCGCCCGCGCCTTCCCCGCCGCCCCCGGCGCCCCCGGCCCCC(SEQ ID NO:1).
CTCACCGCTCCCCGGGGCGGGGCCGCGCCCTCTGAGCGGGGGATGCCGGCCGCG
CCCCGCGACCCCAGCCCCGGGCAGCCCTCTGCGCTCTGGGGGACCCCCGGCGGC
CGTGGCCCGGCGCGCTGAGCTGGTGCTGAAGGGACAGCTCCGGCCGAGCCCCGC
AGCCCCCGCAGCCCCGGGCGGCTCATGGTCCCCGAAGCCGAAGCTGAAGCCCAG
GCCCGGGCGGGGATGCTGGGGATGCCCCGCGGGTGAGGCCCCCGCTGCAGCCGT
GTTCATGGCGGTGGCCAGGAAGATCCGAACTTTGCTGACGGTGAACATCCTGGT
GTTCGTGGGCATCGTCCTGTTCTCCGTGTACTGCCGCCTGCAGGGCCGCTCCCAG
GAGCTCGTGCGCATCGTGAGCGGCGACCGCCGGGTGCGCAGCCGACACGCCAAG
GTGGGCACGCTGGGGGACCGTGAGGCCATCCTGCAGCGCCTGGACCACCTGGAG
GAGGTGGTCTACAACCAGCTCAACGGCCTTGCCAAGCCCATCGGCCTGGTGGAG
GGGCCAGGAGGCCTGGGCCAGGGTGGCTTGGCGGCCACCCTGCGTGATGACGGC
CAGGAGGCGGAAGGCAAGTATGAGGAGTACGGCTACAACGCTCAGCTCAGCGA
CCGCATCTCCCTCGATCGGAGCATCCCCGACTACCGGCCCAGAAAGTGCAGACA
GATGAGCTACGCCCAGGACCTGCCCCAGGTCTCCGTGGTCTTCATCTTCGTCAAT
GAGGCGCTGTCGGTCATCCTGCGCTCCGTGCACAGCGTGGTCAACCACACGCCCT
```

```
CCCAGCTCCTCAAGGAGGTCATCCTGGTGGACGACAACAGTGACAACGTGGAAC

TCAAGTTCAATCTGGACCAGTACGTCAACAAGCGGTACCCAGGCCTCGTGAAGA

TTGTCCGCAACAGCCGGCGGGAAGGACTGATCCGCGCGGCTGCAGGGCTGGA

AGGCGGCCACCGCCCCAGTCGTCGGCTTCTTTGATGCCCACGTCGAGTTCAACAC

GGGCTGGGCCGAGCCCGCACTGTCGCGGATCCGAGAGGACCGGCGTCGCATCGT

GCTGCCAGCCATCGACAACATCAAGTACAGCACGTTTGAGGTGCAGCAGTATGC

GAACGCCGCCCATGGCTACAACTGGGCCTCTGGTGCATGTACATCATCCCCCCG

CAGGACTGGCTGGACCGCGGCGACGAGTCAGCACCCATCAGGACCCCAGCCATG

ATCGGCTGCTCCTTCGTAGTGGACCGCGAGTACTTCGGAGACATTGGGCTGCTGG

ACCCCGGCATGGAGGTGTATGGCGGCGAGAACGTAGAACTGGGCATGAGGGTGT

GGCAGTGTGGCGGCAGCATGGAGGTGCTGCCCTGCTCCCGCGTGGCCCACATCG

AGCGCACCAGGAAGCCCTACAACAACGACATTGACTACTACGCCAAGCGCAACG

CCCTGCGCGCCGCCGAGGTGTGGATGGATGACTTCAAGTCCCACGTGTACATGG

CCTGGAACATCCCCATGTCGAACCCAGGGGTGGACTTCGGGGACGTGTCTGAGA

GGCTGGCCCTGCGTCAGAGGCTGAAGTGTCGCAGCTTCAAGTGGTACCTGGAGA

ACGTGTACCCGGAGATGAGGGTCTACAACAACACCCTCACGTACGGAGAGGTGA

GAAACAGCAAAGCCAGTGCCTACTGTCTGGACCAGGGAGCGGAGGACGGCGAC

CGGGCGATCCTCTACCCCTGCCACGGGATGTCCTCCCAGCTGGTGCGGTACAGCG

CTGACGGCCTGCTGCAGCTGGGGCCTCTGGGCTCCACAGCCTTCTTGCCTGACTC

CAAGTGTCTGGTGGATGACGGCACGGGCCGCATGCCCACCCTGAAGAAGTGTGA

GGATGTGGCGCGGCCAACACAGCGGCTGTGGGACTTCACCCAGAGTGGCCCCAT

TGTGAGCCGGGCCACGGGCCGCTGCCTGGAGGTGGAGATGTCCAAAGATGCCAA

CTTTGGGCTCCGGCTGGTGGTACAGAGGTGCTCGGGGCAGAAGTGGATGATCAG

AAACTGGATCAAACACGCACGGCACTGACCCCACCTCCGCCCGGACCCCCACAG

ACCTCGGGAAGGCGCTGGGCCGAGCCAGTGTGGCTGAGTGACCGGGGTGTGCCC

GGCAGACACAGCAGGACAGGGCTCTATGTGCGGCCAGGACAGCAGAGGCTGAG

GGGCCGGGGTGTGGCTGAGTGACCAGGGTGTCACCCACTGCATCTGGAGTACAG

CTTCTCCTAGGACAGGCGGCTCTACCCGAGGGAGGGCGTCTGGGGACAGTGATG

CCAACTCAAACACGTGCCTTCTCCACGGTATCTCCTGGCCAGGCTGCTGGGACAG

CCGCCGCCTCTGCATGTACCACAGCCCCCACGCCCCATAGGGAGGCCAAGCCC

CGGACCATGCACCAGGCTGCACCCTGGTGTCTTCCACCCGCAGGCCTCCCATGCT

CCAAGCAGCCTCCCCCAGCACTTGCGGCCGC
```

The human 47174 sequence (FIG. 1; SEQ ID NO:1) is approximately 2572 nucleotides long. The nucleic acid sequence includes an initiation codon (ATG) and a termination codon (TGA) which are bolded and underscored above. The region between and inclusive of the initiation codon and the termination codon is a methionine-initiated coding sequence of about 1812 nucleotides, including the termination codon (nucleotides indicated as "coding" of SEQ ID NO:1; SEQ ID NO:3). The coding sequence encodes a 603 amino acid protein (SEQ ID NO:2), which is recited as follows:

MAVARKIRTLLTVNILVFVGIVLFSVYCRLQGRSQELVRIVSGDRRVRSRHAK    (SEQ ID NO:2).

VGTLGDREAILQRLDHLEEVVYNQLNGLAKPIGLVEGPGGLGQGGLAATLRDDGQE

AEGKYEEYGYNAQLSDRISLDRSIPDYRPRKCRQMSYAQDLPQVSVVFIFVNEALSVI

LRSVHSVVNHTPSQLLKEVILVDDNSDNVELKFNLDQYVNKRYPGLVKIVRNSRRE

GLIRARLQGWKAATAPVVGFFDAHVEFNTGWAEPALSRIREDRRRIVLPAIDNIKYS

TFEVQQYANAAHGYNWGLWCMYIIPPQDWLDRGDESAPIRTPAMIGCSFVVDREYF

GDIGLLDPGMEVYGGENVELGMRVWQCGGSMEVLPCSRVAHIERTRKPYNNDIDY

YAKRNALRAAEVWMDDFKSHVYMAWNIPMSNPGVDFGDVSERLALRQRLKCRSF

KWYLENVYPEMRVYNNTLTYGEVRNSKASAYCLDQGAEDGDRAILYPCHGMSSQL

VRYSADGLLQLGPLGSTAFLPDSKCLVDDGTGRMPTLKKCEDVARPTQRLWDFTQS

GPIVSRATGRCLEVEMSKDANFGLRLVVQRCSGQKWMIRNWIKHARH

Example 2
Tissue Distribution of 47174 mRNA

Endogenous human 47174 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a way of quantitating the initial template concentration. Samples can be internally controlled by the addition of a second set of primers/probe specific for a housekeeping gene such as GAPDH which has been labeled with a different fluorophore on the 5' end (typically VIC).

To determine the level of 47174 in various human tissues a primer/probe set was designed using Primer Express (Perkin-Elmer) software and primary cDNA sequence information. Total RNA was prepared from a series of human tissues using an RNeasy kit from Qiagen. First strand cDNA was prepared from 1 µg total RNA using an oligo-dT primer and Superscript II reverse transcriptase (Gibco/BRL). cDNA obtained from approximately 50 ng total RNA was used per TaqMan reaction.

47174 mRNA levels were analyzed in a variety of samples of human tissues. Table 1 below shows the relative level of expression in a number of tissues. The highest level of relative expression is found in normal brain cortex and hypothalamus. 47174 mRNA expression was also detected in normal kidney.

TABLE 1

| SAMPLE | RELATIVE EXPRESSSION |
|---|---|
| Aorta/normal | 0.00 |
| Fetal heart/normal | 0.00 |
| Heart normal | 0.00 |
| Heart/CHF | 0.00 |

TABLE 1-continued

| SAMPLE | RELATIVE EXPRESSSION |
|---|---|
| Vein/Normal | 0.00 |
| Spinal cord/Normal | 0.00 |
| Brain cortex/Normal | 33.96 |
| Brain hypothalamus/Normal | 10.13 |
| Glial cells (Astrocytes) | 0.00 |
| Brain/Glioblastoma | 0.00 |
| Breast/Normal | 0.00 |
| Breast tumor/IDC | 0.00 |
| OVARY/Normal | 0.00 |
| OVARY/Tumor | 0.00 |
| Pancreas | 0.00 |
| Prostate/Normal | 0.00 |
| Prostate/Tumor | 0.00 |
| Colon/normal | 0.00 |
| Colon/tumor | 0.00 |
| Colon/IBD | 0.00 |
| Kidney/normal | 0.66 |
| Liver/normal | 0.00 |
| Liver fibrosis | 0.00 |
| Fetal Liver/normal | 0.00 |
| Lung/normal | 0.00 |
| Lung/tumor | 0.00 |
| Lung/COPD | 0.00 |
| Spleen/normal | 0.00 |
| Tonsil/normal | 0.00 |
| Lymph node/normal | 0.00 |
| Thymus/normal | 0.00 |
| Epithelial Cells (prostate) | 0.00 |
| Endothelial Cells (aortic) | 0.00 |
| Skeletal Muscle/Normal | 0.00 |
| Fibroblasts (Dermal) | 0.00 |
| Skin/normal | 0.00 |
| Adipose/Normal | 0.00 |
| Osteoblasts (primary) | 0.00 |
| Osteoblasts (Undiff) | 0.00 |
| Osteoblasts (Diff) | 0.00 |
| Osteoclasts | 0.00 |
| Aortic SMC Early | 0.00 |

TABLE 1-continued

| SAMPLE | RELATIVE EXPRESSSION |
| --- | --- |
| Aortic SMC Late | 0.00 |
| shear HUVEC | 0.00 |
| static HUVEC | 0.00 |
| Osteoclasts(Undiff) | 0.00 |

Example 3
Northern Blot Hybridizations

Northern blot hybridizations with various RNA samples can also be performed under standard conditions and washed under stringent conditions, i.e., 0.2×SSC at 65° C. A DNA probe corresponding to all or a portion of the 47174 cDNA (SEQ ID NO:1) can be used. The DNA can be radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 4
Recombinant Expression of 47174 in Bacterial Cells

In this example, 47174 is expressed as a recombinant glutathione-S-transferase (GST) fusion polypeptide in *E. coli* and the fusion polypeptide is isolated and characterized. Specifically, 47174 is fused to GST and this fusion polypeptide is expressed in *E. coli*, e.g., strain PEB199. Expression of the GST-47174 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 5
Expression of Recombinant 47174 Protein in COS Cells

To express the 47174 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 47174 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 47174 DNA sequence is amplified by PCR using two primers. The 5' primer contains the restriction site of interest followed by approximately twenty nucleotides of the 47174 coding sequence starting from the initiation codon; the 3' end sequence contains complementary sequences to the other restriction site of interest, a translation stop codon, the HA tag or FLAG tag and the last 20 nucleotides of the 47174 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 47174 gene is inserted in the correct orientation. The ligation mixture is transformed into *E. coli* cells (strains HB 101, DH5, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 47174-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989. The expression of the 47174 polypeptide is detected by radiolabelling (35S-methionine or 35S-cysteine available from NEN, Boston, MA, can be used) and immunoprecipitation (Harlow, E. and Lane, D. Antibodies: A Laboratory Manual, Cold Spring Harbor Laboratory Press, Cold Spring Harbor, N.Y., 1988) using an HA specific monoclonal antibody. Briefly, the cells are labeled for 8 hours with 35S-methionine (or 35S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 47174 coding sequence is cloned directly into the polylinker of the pCDNA/Amp vector using the appropriate restriction sites. The resulting plasmid is transfected into COS cells in the manner described above, and the expression of the 47174 polypeptide is detected by radiolabelling and immunoprecipitation using a 47174 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of identifying a compound which binds to a human glycosyltransferase protein comprising:

a) combining a compound to be tested with a host cell expressing human glycosyltransferase protein having an amino acid sequence as set forth in SEQ ID NO:2 under conditions suitable for binding of said compound to said human glycosyltransferase protein; and b) detecting the formation of a complex between said compound and said human glycosyltransferase protein.

2. The method of claim 1, wherein said method is a competition assay, in which binding is determined in the presence of one or more compounds.

3. The method of claim 1, wherein the formation of a complex is monitored by detecting the synthesis of a glycoconjugate.

4. The method of claim 1, wherein said host cell is a mammalian cell.

5. The method of claim 1, wherein said human glycosyltransferase protein having the amino acid sequence set forth in SEQ ID NO:2 is encoded by the nucleotide sequence set forth in SEQ ID NO:1.

6. The method of claim 5, wherein said method is a competition assay, in which binding is determined in the presence of one or more compounds.

7. The method of claim 5, wherein the formation of a complex is monitored by detecting the synthesis of a glycoconjugate.

8. A method of identifying a compound which binds to a human glycosyltransferase protein comprising:
   a) combining a compound to be tested with a host cell expressing a fusion protein comprising a human glycosyltransferase with SEQ ID NO:2 under conditions suitable for binding of said compound to said human glycosyltransferase protein; and
   b) detecting the formation of a complex between said compound and said fusion protein.

9. The method of claim 8, wherein said method is a competition assay, in which binding is determined in the presence of one or more compounds.

10. The method of claim 8, wherein the formation of a complex is monitored by detecting the synthesis of a glycoconjugate.

11. The method of claim 8, wherein said host cell is a mammalian cell.

12. The method of claim 8, wherein the amino acid sequence set forth in SEQ ID NO:2 is encoded by the nucleotide sequence set forth in SEQ ID NO:1.

13. The method of claim 12, wherein said method is a competition assay, in which binding is determined in the presence of one or more compounds.

14. The method of claim 12, wherein the formation of a complex is monitored by detecting the synthesis of a glycoconjugate.

* * * * *